(12) United States Patent
Rosenthal et al.

(10) Patent No.: US 7,445,629 B2
(45) Date of Patent: Nov. 4, 2008

(54) MEDICAL DEVICE FOR DELIVERING BIOLOGICALLY ACTIVE MATERIAL

(75) Inventors: Arthur Rosenthal, Boston, MA (US); James J. Barry, Marlborough, MA (US); Matthew Miller, White Bear Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/987,284

(22) Filed: Nov. 11, 2004

(65) Prior Publication Data

US 2005/0113903 A1    May 26, 2005

Related U.S. Application Data

(63) Continuation-in-part of application No. 10/062,794, filed on Jan. 31, 2002, now Pat. No. 7,291,165.

(51) Int. Cl.
*A61F 2/06* (2006.01)
(52) U.S. Cl. ....................................................... 623/1.42
(58) Field of Classification Search ........ 623/1.11–1.42
See application file for complete search history.

(56) References Cited

U.S. PATENT DOCUMENTS 4,655,771 A    4/1987    Wallsten (Continued)

FOREIGN PATENT DOCUMENTS

EP         1 103 234 A1    5/2001

(Continued)

OTHER PUBLICATIONS

Alexander, *Slack, Incorporated Newspaper*, http://slackinc.com/general/cardio/199811/candywrap.asp.

(Continued)

*Primary Examiner*—Suzette Gherbi
(74) *Attorney, Agent, or Firm*—Vidas, Arrett & Steinkraus

(57) ABSTRACT

This invention relates generally to medical devices, such as stents, for delivering a biologically active material to a desired location within the body of a patient. In particular, the invention relates generally to a medical device for delivering a biologically active material to a surface of a body lumen. More particularly, the invention is directed to a medical device comprising two opposing end sections, each having a surface, and a middle portion. The middle portion comprises a plurality of struts and the two opposing end sections comprises non-structural elements. The end sections of the surface either (1) contain a greater amount of a biologically active material per unit length of the surface or (2) have a greater capacity per unit length to contain such material than the middle section of the surface by having a greater surface area per unit length of the surface than the middle section or having a greater affinity for the biologically active material per unit length of the surface than the middle section. The struts and the non-structural elements comprise biologically active materials. The invention is also directed to a method for delivering the biologically active material to the body tissue of a patient by inserting this medical device into the body of the patient. Still further, the invention is directed to a method of treating a body lumen surface by preventing or treating restenosis or hyperplasia, using the system of the invention. Still further, the invention is directed to a stent having a sidewall which comprises a middle section, a first end section and a second end section. The stent also comprises a band comprising a biologically active material. The band is connected to the first end section and/or second end section of the stent.

24 Claims, 13 Drawing Sheets

U.S. PATENT DOCUMENTS

| | | | |
|---|---|---|---|
| 4,728,328 A | 3/1988 | Hughes et al. | |
| 4,733,665 A | 3/1988 | Palmaz | |
| 4,800,882 A | 1/1989 | Gianturco | |
| 4,886,062 A | 12/1989 | Wiktor | |
| 4,954,126 A | 9/1990 | Wallsten | |
| 5,061,275 A | 10/1991 | Wallsten et al. | |
| 5,064,435 A | 11/1991 | Porter | |
| 5,336,518 A | 8/1994 | Narayanan et al. | |
| 5,356,433 A | 10/1994 | Rowland et al. | |
| 5,449,373 A | 9/1995 | Pinchasik et al. | |
| 5,522,881 A * | 6/1996 | Lentz | 623/1.13 |
| 5,609,629 A | 3/1997 | Fearnot et al. | |
| 5,643,309 A | 7/1997 | Myler et al. | |
| 5,667,523 A | 9/1997 | Bynon et al. | |
| 5,693,085 A * | 12/1997 | Buirge et al. | 623/1.13 |
| 5,725,572 A | 3/1998 | Lam et al. | |
| 5,746,691 A | 5/1998 | Frantzen | |
| 5,799,384 A | 9/1998 | Schwartz et al. | |
| 5,817,126 A | 10/1998 | Imran | |
| 5,824,045 A | 10/1998 | Alt | |
| 5,824,049 A | 10/1998 | Ragheb et al. | |
| 5,843,172 A | 12/1998 | Yan | |
| 6,004,346 A | 12/1999 | Wolff et al. | |
| 6,033,381 A | 3/2000 | Kontos | |
| 6,083,257 A | 7/2000 | Taylor et al. | |
| 6,087,479 A | 7/2000 | Stamler et al. | |
| 6,099,562 A | 8/2000 | Ding et al. | |
| 6,106,548 A | 8/2000 | Roubin et al. | |
| 6,192,271 B1 | 2/2001 | Hayman | |
| 6,197,013 B1 | 3/2001 | Reed et al. | |
| 6,254,632 B1 | 7/2001 | Wu et al. | |
| 6,273,913 B1 | 8/2001 | Wright et al. | |
| 6,287,628 B1 | 9/2001 | Hossainy et al. | |
| 6,299,604 B1 | 10/2001 | Ragheb et al. | |
| 6,325,825 B1 | 12/2001 | Kula et al. | |
| 6,375,787 B1 | 4/2002 | Lukic | |
| 6,379,379 B1 | 4/2002 | Wang | |
| 6,379,382 B1 | 4/2002 | Yang | |
| 6,383,215 B1 | 5/2002 | Sass | |
| 6,428,570 B1 | 8/2002 | Globerman | |
| 6,451,050 B1 | 9/2002 | Rudakov et al. | |
| 6,458,152 B1 | 10/2002 | Khosravi et al. | |
| 6,471,979 B2 | 10/2002 | New et al. | |
| 6,471,980 B2 | 10/2002 | Sirhan et al. | |
| 6,488,701 B1 | 12/2002 | Nolting et al. | |
| 6,506,437 B1 | 1/2003 | Harish et al. | |
| 6,517,889 B1 | 2/2003 | Jayaraman | |
| 6,540,777 B2 | 4/2003 | Stenzel | |
| 6,562,065 B1 | 5/2003 | Shanley | |
| 6,613,083 B2 | 9/2003 | Alt | |
| 6,652,575 B2 | 11/2003 | Wang | |
| 6,656,216 B1 | 12/2003 | Hossainy et al. | |
| 6,716,242 B1 * | 4/2004 | Altman | 623/1.42 |
| 6,764,505 B1 | 7/2004 | Hossainy et al. | |
| 6,764,507 B2 | 7/2004 | Shanley et al. | |
| 6,776,793 B2 * | 8/2004 | Brown et al. | 623/1.15 |
| 6,786,919 B1 * | 9/2004 | Escano et al. | 623/1.13 |
| 6,863,685 B2 | 3/2005 | Davila et al. | |
| 6,981,985 B2 | 1/2006 | Brown et al. | |
| 6,989,071 B2 | 1/2006 | Kocur et al. | |
| 7,018,401 B1 | 3/2006 | Hyodoh et al. | |
| 7,128,756 B2 | 10/2006 | Lowe et al. | |
| 2002/0007102 A1 | 1/2002 | Salmon et al. | |
| 2002/0107563 A1 | 8/2002 | Shanley | |
| 2002/0183581 A1 | 12/2002 | Yoe et al. | |
| 2003/0064965 A1 | 4/2003 | Richter | |
| 2003/0069630 A1 | 4/2003 | Burgermeister et al. | |
| 2003/0083646 A1 | 5/2003 | Sirhan et al. | |
| 2004/0006382 A1 | 1/2004 | Sohier | |
| 2004/0098117 A1 | 5/2004 | Hossainy et al. | |
| 2004/0099118 A1 * | 5/2004 | Granada et al. | 623/1.42 |
| 2004/0191404 A1 | 9/2004 | Hossainy et al. | |
| 2005/0038497 A1 | 2/2005 | Neuendorf et al. | |
| 2006/0100695 A1 | 5/2006 | Peacock, III et al. | |
| 2006/0224234 A1 * | 10/2006 | Jayaraman | 623/1.16 |
| 2007/0073385 A1 * | 3/2007 | Schaeffer et al. | 623/1.16 |
| 2007/0135897 A1 | 6/2007 | Chen et al. | |

FOREIGN PATENT DOCUMENTS

| | | |
|---|---|---|
| WO | WO 94/16646 | 8/1994 |
| WO | WO 98/36784 | 8/1998 |
| WO | WO 03/063924 | 8/2003 |
| WO | WO 2004/049918 | 6/2004 |

OTHER PUBLICATIONS

Creel, *Circulation Research*, Apr. 28, 2000 pp. 879-884 (http://www.circresaha.org).

Farb et al., *Circulation*, Jul. 24, 2001, pp. 473-479 (http://www.circulationaha.org).

Hwang et al., *Circulation*, Jul. 31, 2001, pp. 600-605 (http://www.circulationaha.org).

Insner, *American College of Cardiology 48th Annual Scientific Session*, Mar. 7-10, 1999.

Nikol et al., *Journal of Invasive Cardiology*, 10(8): 506-514, 1998 (http://www.medscape.com/HMP/JIC/1998/v10.n08/jic1008.16.niko-01.html).

Rajani, *BHJ*, (http://www.bhj.org/journal/1999_4102_apr99?sp_228.htm).

Sigwart, *Lancet*. Jul. 24, 1999, (http://www.findarticles.com/cf_0/m0833/9175_354/55404149/pl/article.jhtml).

Albiero et al., European high-activity $^{32}$P radioactive stent experience. *J Invasive Cardiol*. Aug. 2000;12(8):416-21.

Kim et al., Edge stenosis and geographical miss following intracoronary gamma radiation therapy for in-stent restenosis. *J Am Coll Cardiol*. Mar. 15, 2001;37(4):1026-30.

Latchem et al., Beta-radiation for coronary in-stent restenosis. *Catheter Cardiovasc Interv*. Dec. 2000;51(4):422-9.

PCT International Search Report, Int'l Applicaiton No. PCT/US2005/040822; Aug. 11, 2005.

Peng et al., "Role of polymers in improving the results of stenting in coronary arteries", Biomaterials 17(7):685-694 (1996).

* cited by examiner

MEDICAL DEVICE FOR DELIVERING BIOLOGICALLY ACTIVE MATERIAL

This is a continuation-in-part of co-pending U.S. patent application Ser. No. 10/062,794, filed Jan. 31, 2002, which is incorporated herein by reference.

1. FIELD OF THE INVENTION

This invention relates generally to medical devices, such as stents, for delivering a biologically active material to a desired location within the body of a patient. In particular, the invention relates generally to a medical device for delivering a biologically active material to a surface of a body lumen. More particularly, the invention is directed to a medical device comprising a plurality of struts and a plurality of non structural elements integral with the struts, wherein the struts and the non-structural elements comprise the biologically active material. The invention is also directed to a method for delivering the biologically active material to body tissue of a patient by inserting this medical device into body of the patient, and further a method for designing such medical device. The invention is also directed to a medical device comprising a plurality of struts and having an outer surface wherein the outer surface which has a middle section and end sections. The end sections of the outer surface either (1) contain a greater amount of a biologically active material per unit length of the outer surface or (2) have a greater capacity per unit length to contain such material than the middle section of the outer surface by having a greater surface area per unit length of the outer surface than the middle section or having a greater affinity for the biologically active material per unit length of the outer surface than the middle section. The struts and the non-structural elements comprise biologically active materials. The invention is also directed to a method for delivering the biologically active material to the body tissue of a patient by inserting this medical device into the body of the patient. Still further, the invention is directed to a method of treating a body lumen surface by preventing or treating restenosis or hyperplasia, using the system of the invention. Moreover, the invention is directed to a stent having a sidewall which comprises a middle section, a first end section and a second end section. The stent also comprises a band comprising a biologically active material. This band is connected to the first end section and/or the second end section of the stent.

2. BACKGROUND OF THE INVENTION

A variety of medical conditions have been treated by introducing an insertable medical device having a coating for release of a biologically active material. For example, various types of biologically active material-coated medical devices, such as stents, have been proposed for localized delivery of the biologically active material to a body lumen. See, e.g., U.S. Pat. No. 6,099,562 to Ding et al. However, it has been noted that, with existing coated medical devices, the release profile of a biologically active material may not be uniform along the entire length of the medical device.

For example, even if a biologically active material having a pharmacological effect is delivered to a body tissue, such effect may not result if the concentration of the biologically active material in the body tissue is below a certain concentration. Such concentration is referred to as the minimum effective concentration ($C_{min}$) of the biologically active material in the body tissue. Each biologically active material has different $C_{min}$. $C_{min}$ of a biologically active material also varies depending on the type of body tissue to which it is delivered. On the other hand, a biologically active material becomes toxic if its concentration is higher than a certain concentration. Such concentration is referred to as the maximum effective concentration $C_{max}$. In addition, it is insufficient that the mean concentration of the biologically active material delivered through out the body tissue to be treated is greater than $C_{min}$ and smaller than $C_{max}$. The concentration of the biologically active material at each and every area throughout the body tissue to be treated should be equal to or greater than $C_{min}$ but equal to or smaller than $C_{max}$ of the biologically active material. For instance, when a coated stent comprised of struts, such as the stent shown in FIG. 1, is used as a medical device for delivering a hydrophobic biologically active material, concentrations of the biologically active material may significantly differ between the regions of the tissue adjacent to the struts and the regions of the tissue farther from the struts. See Hwang et al., http://www.circulationaha.org (accepted in April 2001). Even if the mean concentration of the biologically active material in the tissue surrounding the stent is above $C_{min}$ of the biologically active material and at or under $C_{max}$, the concentrations at certain regions of the tissue to be treated, which are farther from the struts, may not reach $C_{min}$. Also, if the amount of the biologically active material in the coating is increased to achieve a concentration higher than $C_{min}$ at all regions of the tissue to be treated, then the concentrations at regions of the tissue adjacent to the struts may exceed the toxic levels, as explained below using the figures.

In FIG. 1, the coated stent 10 is placed in a blood vessel 15 having a vessel wall 12 to be treated. This vessel wall is surrounded by tissue 12a. The biologically active material coated on struts 13 of the stent 10 is released into the vessel wall 12 to be treated. FIG. 2 is a cross sectional view along line A of the stent 10 in FIG. 1. FIG. 2 also shows the concentration levels of the biologically active material in each area surrounding the struts 13 at a certain time after the insertion of the stent into the vessel 15. The area adjacent to the struts, i.e., the area between the struts 13 and line 16, has a concentration level at or below $C_{max}$, which is just below the toxic level. The farther from the struts 13 the tissue to be treated is located, the lower the concentration of biologically active material delivered to the tissue becomes. However, the area between line 18 and line 19 has the concentration level at or higher than $C_{min}$. A concentration of the biologically active material in the area outside line 19 is below $C_{min}$.

Also, FIGS. 2A and 2B clearly show that there are gaps between each strut 13 wherein the vessel wall to be treated does not receive sufficient biologically active material to have $C_{min}$. The areas within line 19, i.e., having concentrations above $C_{min}$, may be increased in size to include more area of the vessel wall to be treated 12, if the amount of the biologically active material on the struts 13 is increased. However, by doing so, the concentration of the biologically active material in the area adjacent to the struts 13 may exceed the toxic level. Accordingly, there is a need for a medical device comprising a plurality of struts that can achieve the biologically active material concentration that is above $C_{min}$ and below toxic levels throughout the tissue.

However, exposure to a medical device which is implanted or inserted into the body of a patient can cause the body tissue to exhibit adverse physiological reactions. For instance, the insertion or implantation of certain catheters or stents can lead to the formation of emboli or clots in blood vessels. Other adverse reactions to vascular intervention include endothelial and smooth muscle cell proliferation which can lead to hyperplasia, restenosis, i.e., the re-occlusion of the artery, occlusion of blood vessels, platelet aggregation, and calcification. Restenosis is caused by an accumulation of extracellular matrix containing collagen and proteoglycans in association with smooth muscle cells which is found in both the atheroma and the arterial hyperplastic lesion after balloon injury or clinical angioplasty. Treatment of restenosis often involves a second angioplasty or bypass surgery. The drawbacks of such treatment, including the risk of repeat restenosis, are obvious.

When considering treatment using biologically active material eluting stents, there are several considerations. Firstly, implantation of a drug eluting stent requires precise placement of the stent so that the lesion covered by the stent includes a sufficient margin beyond the angiographically identified lesion boundaries. Hence, even with very careful placement of the stent, it is possible to miss or undertreat the lesion. Secondly, even if a lesion appears to be fully covered by a biologically active material coated stent, balloon injury caused during implantation may extend well beyond the ends of the stent. In the case where such injury can be visualized by angiography, an additional stent may be placed to cover this injury. However, implantation of a second stent may cause further injury in a similar fashion to placement of the first stent. Thirdly, even if there is no evidence of angiographic injury, there may be a zone of biological injury that is well beyond the ends of the stent.

Other problems with the current technology, in particular radioactive stents, is that restenosis may still occur at the parts of the surface of the body lumen that are in contact with the ends of a stent. Closure or constriction of the vessels commonly occurs when the vascular cells proliferate around the ends of the stent. This is known as the "candy-wrapper effect", also known as edge restenosis or edge effect. Albiero et al., 2000, J. Invas. Cardiol. 12(8):416-421; Latchem et al., 2000, Catheter Cardiovasc Interv. 51(4):422-429; Kim et al., 2001, J. Am. Coll. Cardiol. 37(4):1026-1030. A schematic diagram describing this effect is show in FIG. 25. FIG. 25 shows a cross section of a body lumen with a stent implant where restenosis occurred at the opposing ends of the stent. The surface 10 of a body lumen 30 at the ends of the implanted stent 40 is surrounded by hyperproliferating tissues 20. This appearance is similar to a candy with a wrapper and thus the name "candy-wrapper effect". A cause for some types of hyperplasia is that when a body lumen is treated with radiation, the radioactive source is usually targeted towards the center of the stent where the original lesion was situated. In an effort to minimize extraneous radiation to healthy vessel tissue, radiation is targeted towards the center. Hence, restenosis may still occur at the edge of the stent due to a lower dosage of radiation at the ends. The underlying mechanism for this effect is that the radiation dosage at the ends is at a level such that it stimulates cell growth as opposed to stopping it. Clearly, there remains a great need for therapies directed to the prevention and treatment of restenosis and related disorders.

The edge-effect also can occur with non-radioactive stents. With existing coated medical devices, generally, the coating of the biologically active material is uniformly applied along the entire length of the device or surface of the device. For example, conventional coated stents are coated uniformly along the entire length of the surface of the device. The biologically active material-concentration-profile in the body lumen along the length of the coated surface may be in the shape of a bell-curve, wherein the amount of the biologically active material released at the middle of the surface causes a greater tissue concentration than the amount of the biologically active material released at the ends of the coated surface. This uneven concentration-profile in the body lumen along the length of the coated surface may lead to the application of an inadequate or sub-optimal dosage of the biologically active material to the body tissue located at the ends of the coated surface. It is possible that such uneven local concentration of the biologically active material in the wall of the body lumen along the length of the coated surface of the medical device may lead to undesired effects. For example, in the case of a biologically active material-coated stent used to prevent or treat restenosis, if the amount of biologically active material delivered to the tissue located at the ends of the stent is sub-optimal, it is possible that restenosis may occur in such tissue.

The biologically active material dosage at the tissue located at the ends of the coated surface of the medical device can be increased if the concentration or amount of the biologically active material is increased along the entire length of the surface. However, by increasing the concentration or amount of biologically active material released along the entire surface, the dosage delivered to tissue located at the middle of the surface may be too great or even at toxic levels.

Thus, there is a need for a medical device that allows precise placement of the stent with respect to the lesion, a more uniform concentration-profile for biologically active material along the entire length of a coated surface of a medical device, and provide a means for therapeutic concentration of biologically active material at and beyond the physical ends of an implanted stent. This invention avoids the possibility of undesired effects and in particular, preventing intimal hyperplasia and smooth muscle cell proliferation which cause stenosis or restenosis of the body lumen caused by an uneven biologically active material concentration-profile.

Moreover, medical devices wherein a biologically active material is uniformly coated on the entire outer surface of the medical devices that is exposed to body tissue are generally used to deliver such biologically active material to specific parts of such body tissue. For instance, such devices are used to treat lesions in body lumen. However, because the entire outer surface of the device contains the biologically active material, this biologically active material will be delivered to healthy body tissue in addition to the lesion. Treatment of healthy tissue with the biologically active material is not only unnecessary but maybe harmful. Accordingly, there is a need for a medical device that can realize an asymmetry release profile of biologically active material to deliver such material to only a limited region of the body tissue that requires the biologically active material.

Citation of references hereinabove shall not be construed as an admission that such references are prior art to the present invention.

3. SUMMARY OF THE INVENTION

These and other objectives are accomplished by the present invention. To achieve the aforementioned objectives, we have invented a medical device for delivering a biologically active material into a body tissue of a patient; a method for designing such device; and a method for delivery of a biologically active material to a body tissue.

The medical device of the invention is a medical device for delivery of biologically active materials to a body tissue of a patient in need of treatment. The medical device comprises struts and non-structural elements integral with the struts, and those struts and non-structural elements comprise the biologically active material. In an embodiment, the non-structural elements project from the struts and are configured in a shape selected from the group consisting of a cone, a truncated cone, an oval, a straight rod, a bent rod, and a rod having heads at the ends. In another embodiment, the non-structural elements are configured in a shape selected from the groups consisting of hoops, knots and bends, which are located along the stents. In yet another embodiment, the medical device comprises a tubular portion having an outer surface, and the non-structural elements are distributed throughout the outer surface. In another embodiment, the non-structural elements are located in a radially asymmetric distribution on the outer surface. For example, the non-structural elements are distributed in a rectangular portion of the outer surface, or the rectangular portion is parallel to longitudinal axis of the tubular portion. The rectangular portion and the tubular portion may have same length. The surface area of the rectangular portion may be from about 25% to about 75% of the entire surface area of the outer surface. In yet another embodiment, the outer surface has end sections and a middle section, and the end sections comprise a greater number of the non-structural elements per unit length of the outer surface than the middle section. In another embodiment, the biologically active material is selected from the group consisting of paclitaxel, actinomycin, sirolimus, tacrolimus, everolimus, dexamethasone, halofuginone and hydrophobic nitric oxide adducts.

The present invention is also directed to a method for delivering a biologically active material to body tissue of a patient which comprises inserting the above-mentioned medical device into the body of the patient.

Further, the present invention is directed to a method for designing such medical device, such as a stent, for delivering a biologically active material to a body tissue of a patient, wherein the medical device comprises a plurality of struts and a plurality of non-structural elements integral with the struts, wherein the struts and the non-structural elements comprise the biologically active material. The method comprises: (a) providing a preliminary medical device comprising struts in a geometric pattern wherein the struts comprise the biologically active material; (b) determining a concentration-profile for the biologically active material which is released from the preliminary medical device; and (c) modifying the geometric pattern of the struts of the preliminary medical device by incorporating non-structural elements comprising the biologically active material that are integral with the struts to achieve more desired distribution of the biologically active material in the body tissue. In an embodiment, the biologically active material has a minimum effective concentration and a maximum effective concentration for the body tissue, and wherein steps (b) and (c) are repeated until the body tissue to be treated is substantially free from a concentration of the biologically active material that is smaller than the minimum effective concentration and a concentration of the biologically active material that is greater than the maximum effective concentration over a desired time period. In another embodiment, the biologically active material is selected from the group consisting of paclitaxel, actinomycin, sirolimus, tacrolimus, everolimus, dexamethasone, halofuginone and hydrophobic nitric oxide adducts.

The present invention is also directed to a medical device such as a stent that is insertable into the body of a patient. The medical device has an outer surface comprising struts, and the outer surface has a middle section and end sections. The end sections have a greater available surface area per unit length of the outer surface than the middle section. In one embodiment, at least a part of each of the middle section and the end sections have greater affinity for the biologically active material per unit length of the outer surface than the middle section. In yet another embodiment, the end sections have a greater amount of the biologically active material per unit length of the outer surface than the middle section. Further, in another embodiment, at least a part of each of the middle section and the end sections is covered with a coating comprising the biologically active material, and the middle section comprises a barrier layer placed over the coating covering the middle section. In another embodiment, the end sections have a greater surface area by having a more porous surface than struts located at the middle section. The struts located at the end sections are comprised of a porous material and the struts located at the middle section is comprised of a less porous material. The struts located at the end sections are covered with the porous material, and the struts located at the middle section are covered with the less porous material. The average diameter of the struts located at the end sections is greater than the average diameter of the struts located at the middle section.

Moreover, the present invention provides, another embodiment of the medical device for treating body tissue. The medical device comprises an outer surface comprising struts. The outer surface has a rectangular portion having a greater capacity for carrying or containing a biologically active material per unit length of the outer surface than the parts of the outer surface that are outside the rectangular portion. In the alternative, the rectangular portion may have a greater affinity for the biologically active material. The present invention is also directed to a method for delivering a biologically active material by inserting the above mentioned medical device comprising the biologically active material in such a way that the rectangular portion is in direct contact with the body tissue in need of treatment.

In another embodiment, the end sections have greater affinity for the biologically active material per unit length of the outer surface than the middle section. At least a part of each of the middle section and the end sections of the outer surface comprise the biologically active material. The struts located at the end sections comprise a first matrix material and the struts located at the middle section comprise a second matrix material, and wherein the first matrix material has a greater affinity for the biologically active material than the second matrix material. The struts located at the end sections are covered with a coating of the first matrix material and the struts located at the middle section are covered with a coating of the second matrix material. The end sections and middle section further comprise the biologically active material.

At least a part of each of the middle section and the end sections are covered with a linking material, and wherein the struts located at the end sections comprise a greater amount of the linking material per unit length of the outer surface than the struts located at the middle section. The outer surface comprises the biologically active material which is linked to the linking material.

In yet another embodiment, the end sections have a greater amount of the biologically active material per unit length of the outer surface than the middle section. The present invention is further directed to a medical device insertable into the body of a patient, which comprises an outer surface, wherein the outer surface has a middle section and end sections, wherein at least a part of each of the middle section and the end sections is covered with a coating layer comprising a first biologically active material, and wherein the end sections carry or contain a larger amount of first biologically active material per unit length of the outer surface than the middle section. The medical device may comprise a tubular portion that comprises the outer surface. The coating covering the end sections may further comprise a coating layer containing a second biologically active material.

In another embodiment, the present invention provides a medical device comprising a sidewall and a first band comprising a first biologically active material. The sidewall of the medical device has a middle section, a first end section and a second end section. The first band is connected to the first end section. In another embodiment, a second band is connected to the second end section.

In another embodiment, the present invention provides a medical device comprising a middle section, a first and second end sections. The first and second end sections each comprise an edge and the first band comprises an inner end. The first band is connected to the first end section such that the first band inner end is adjacent to the first end section edge.

4. BRIEF DESCRIPTION OF THE DRAWINGS

FIGS. 2A and 2B also show areas of body tissue having different concentration levels of the biologically active material.

FIGS. 4A and 4B also show areas having different concentration levels of the biologically active material.

FIGS. 6-14, each depicts struts having non-structural elements integral with the struts.

Figure 15:
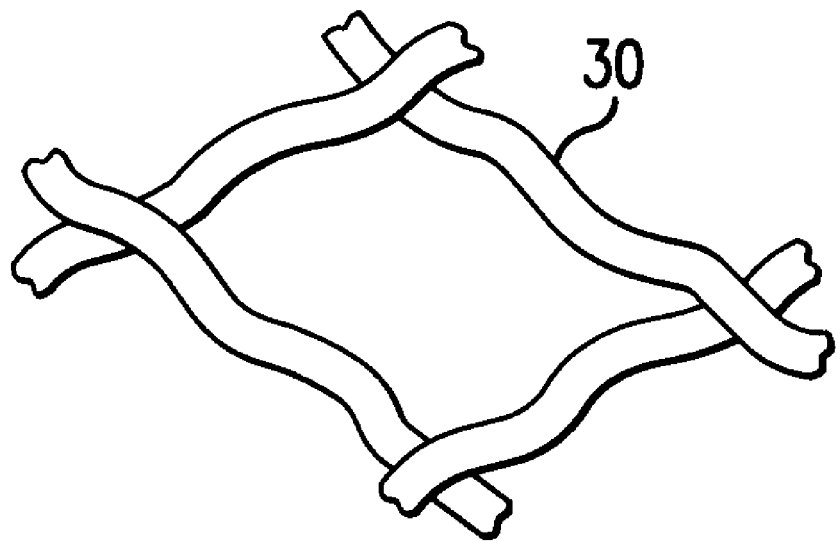

FIG. 15 depicts wavy struts that have greater surface area per unit length of the strut than conventional struts.

Figure 16:
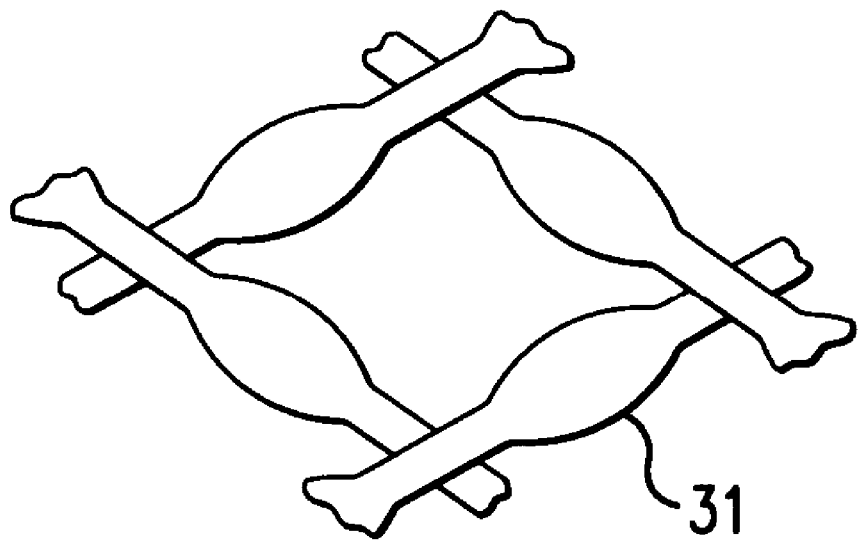

FIG. 16 depicts struts having a greater average diameter per length of the strut than the conventional struts.

Figure 17:
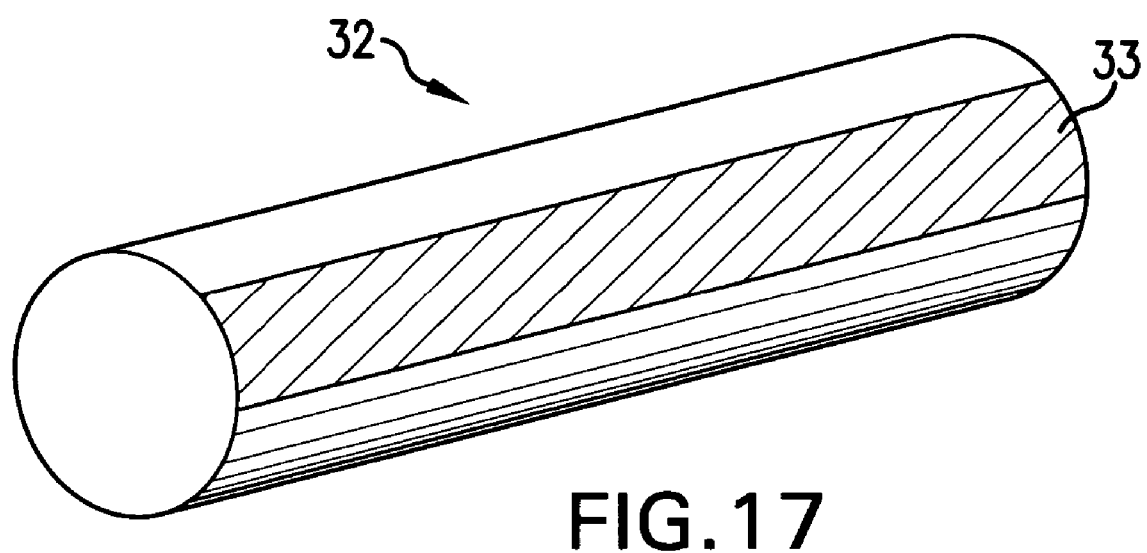

FIG. 17 depicts a simplified view of a stent having a rectangular portion of the outer surface where non-structural elements are located, and the rectangular portion is shown by hatching.

Figure 18:
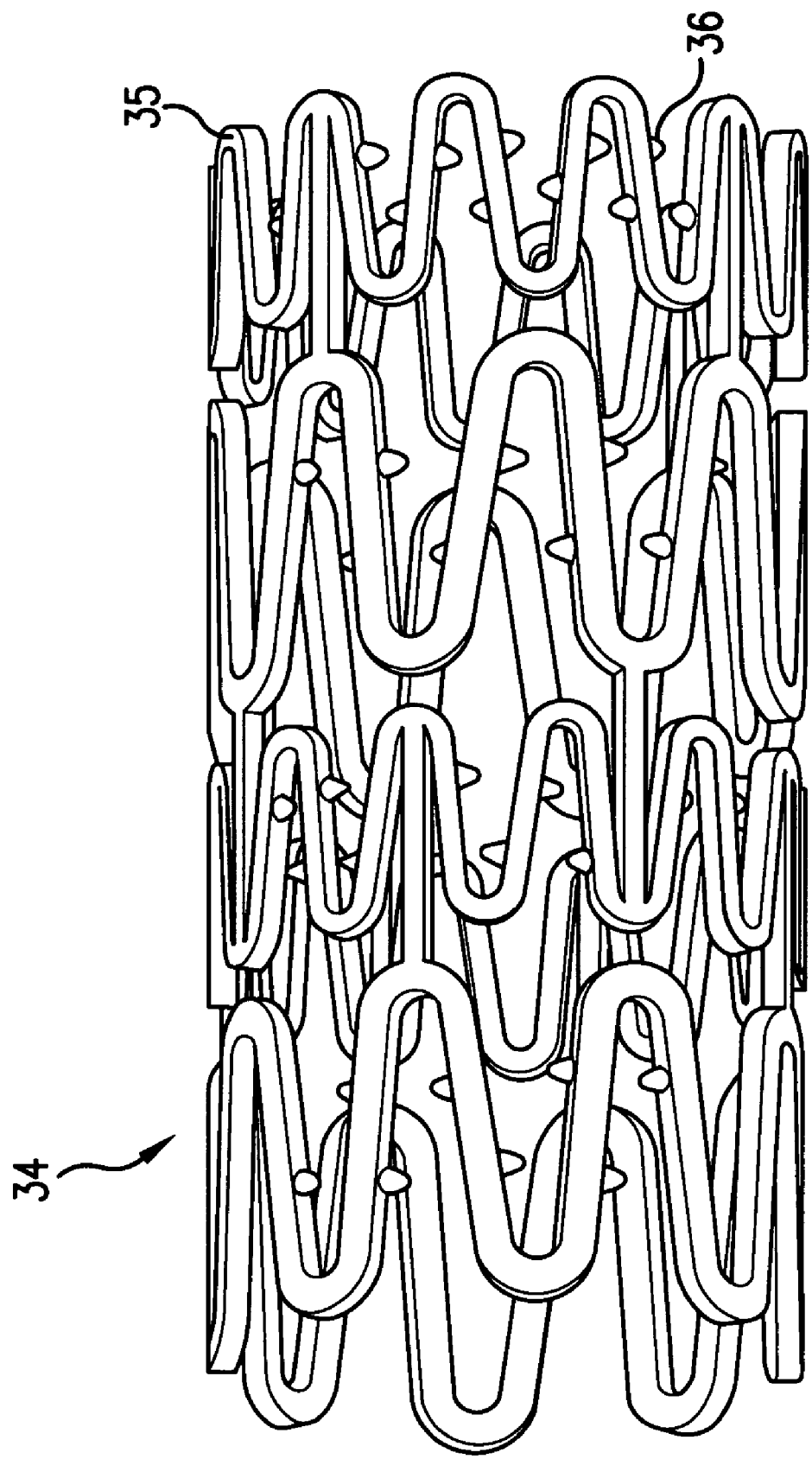

FIG. 18 depicts a perspective view of a stent wherein non-structural elements are located only in a rectangular portion of the outer surface.

Figure 19:
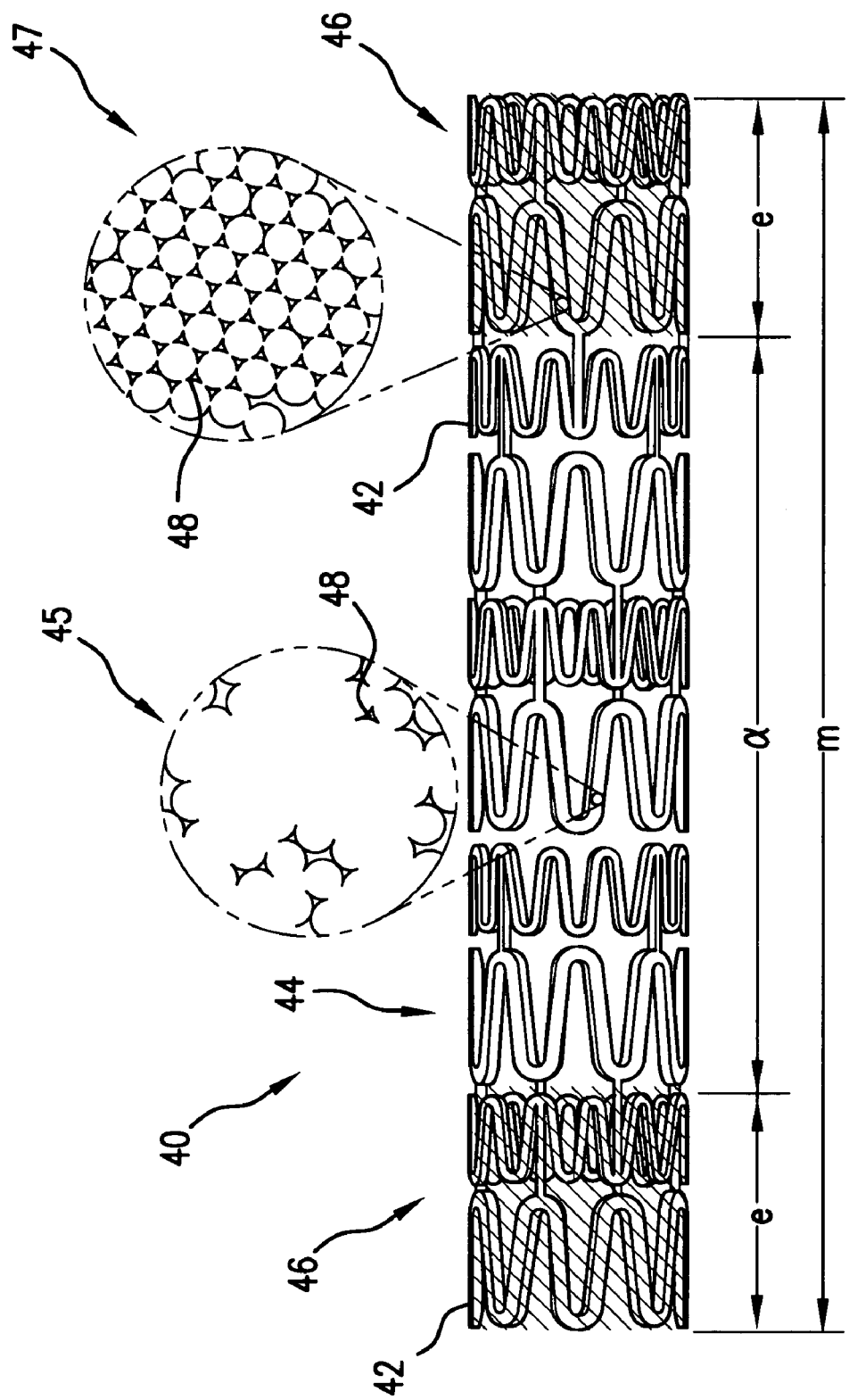

FIG. 19 depicts a stent having end sections and a middle section and comprised of struts, wherein the end sections are comprised of a porous material and the middle section is comprised of a less porous material.

Figure 20:
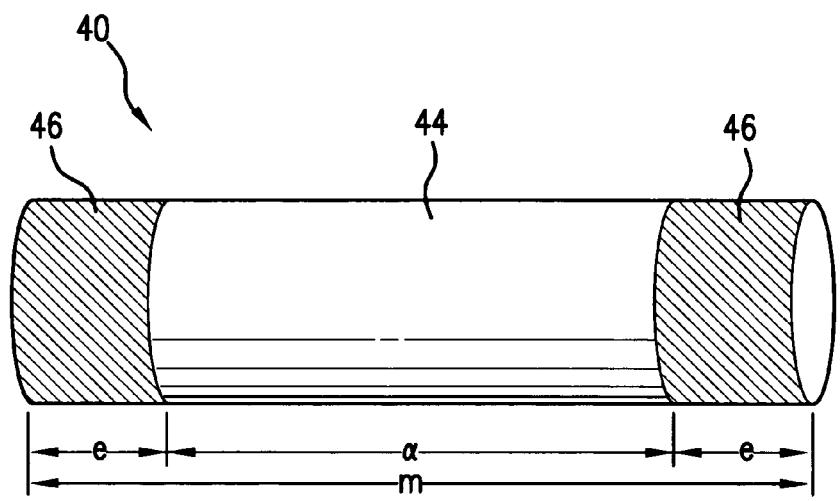

FIG. 20 is a simplified view of a stent which shows the outer surface, having end sections and a middle section.

Figure 21:
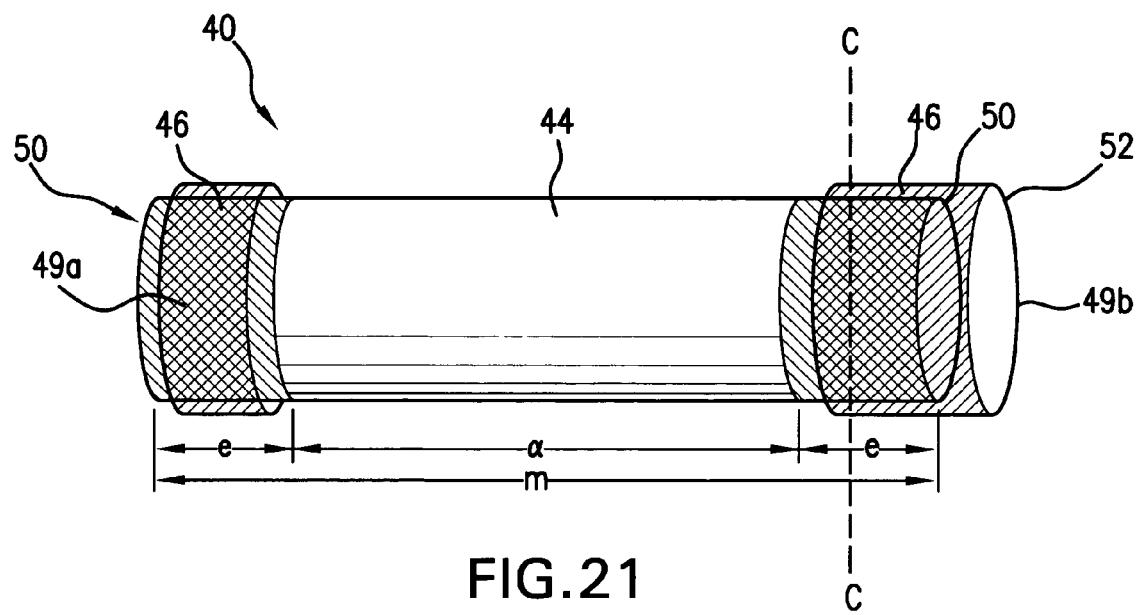

FIG. 21 is a simplified view of a stent having bands attached to end sections of the stent.

Figure 22:
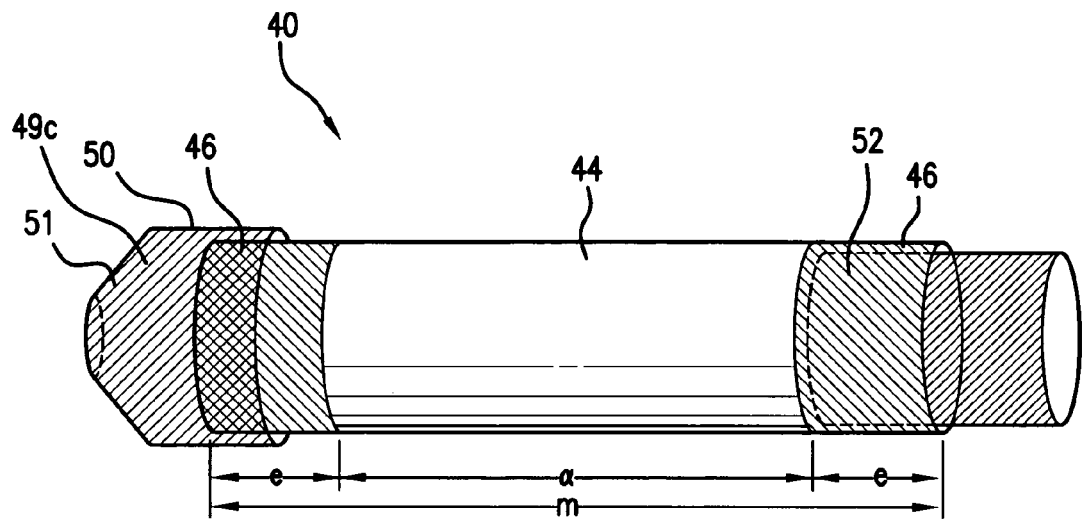

FIG. 22 is a simplified view of a stent having bands attached to end sections of the stent.

Figure 23:
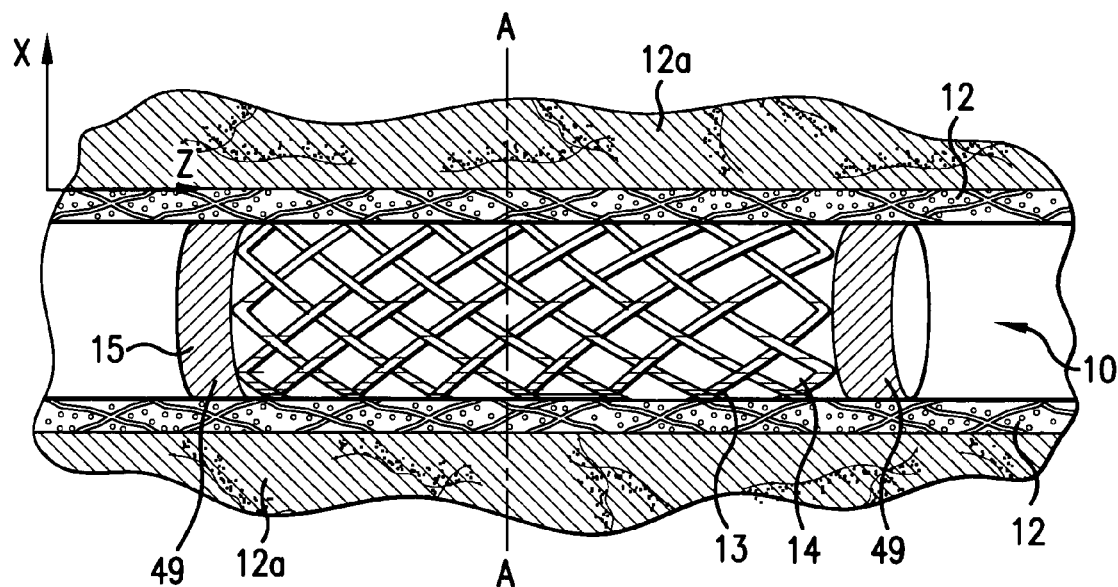

FIG. 23 is a simplified view of a stent having bands attached to end sections of the stent which is implanted in a lumen.

Figure 24:
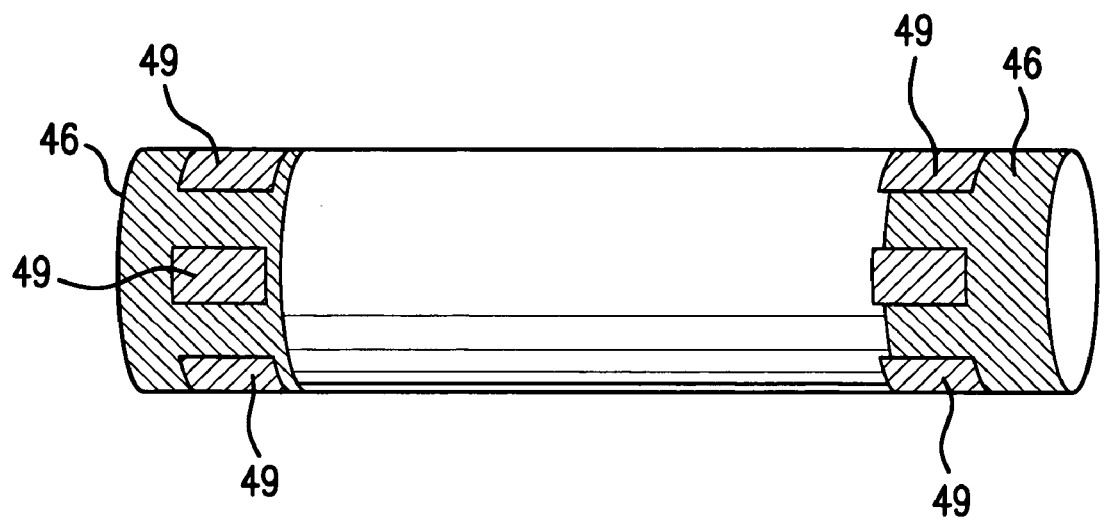

FIG. 24 is a simplified view of a stent having bands attached to part of the circumference of the end sections of the stent.

Figure 25:
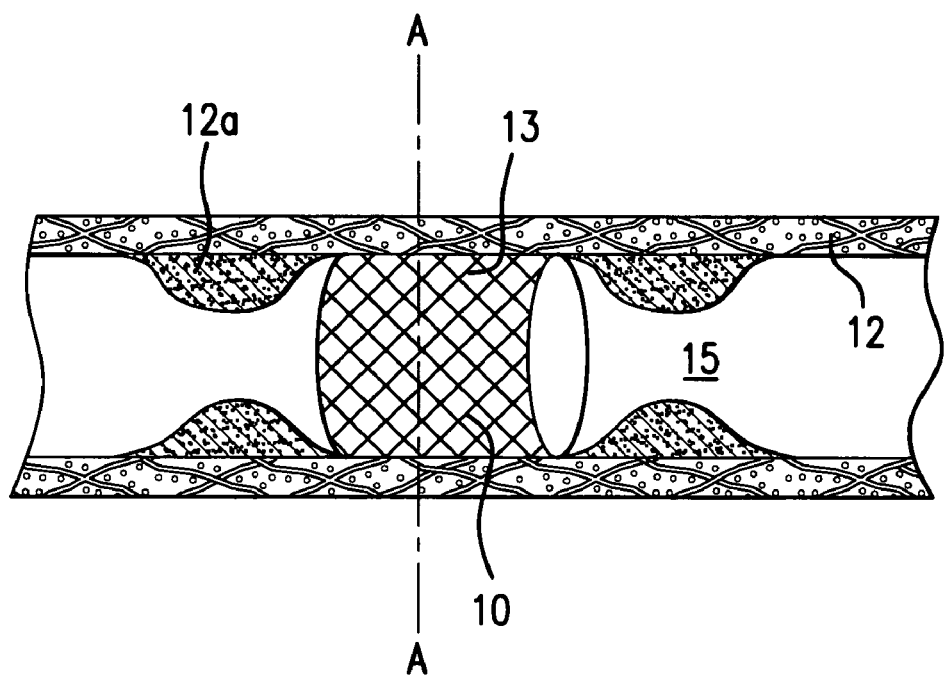

FIG. 25 is a simplified view of a stent implanted in a lumen in which the edge effect is illustrated.

5. DETAILED DESCRIPTION OF THE INVENTION

5.1. Medical Device for Delivering Biologically Active Material with Desired Distribution

5.1.1. Non-Structural Elements

Even if a biologically active material having a pharmacological effect is delivered to a body tissue, such effect may not result if the concentration of the biologically active material in the body tissue is below a certain concentration. Such concentration is referred to as the minimum effective concentration ($C_{min}$) of the biologically active material in the body tissue. Each biologically active material has different $C_{min}$. $C_{min}$ of a biologically active material also varies depending on the type of body tissue to which it is delivered. On the other hand, a biologically active material becomes toxic if its concentration is higher than a certain concentration. Such concentration is referred to as the maximum effective concentration $C_{max}$. In addition, it is insufficient that the mean concentration of the biologically active material delivered through out the body tissue to be treated is greater than $C_{min}$ and smaller than $C_{max}$. The concentration of the biologically active material at each and every area throughout the body tissue to be treated should be equal to or greater than $C_{min}$ but equal to or smaller than $C_{max}$ of the biologically active material.

When the medical device is comprised of a plurality of struts comprising a biologically active material, the body tissue located at or near a center of each "cell" of the medical device, i.e., openings between the struts, tends to have the lowest concentration of the biologically active material. Such concentration can be below $C_{min}$. This is particularly true when the biologically active material is hydrophobic. When the concentration of the biologically active material in the tissue located at the center of each cell is lower than $C_{min}$, the concentration can be increased by increasing the amount of the biologically active material coated on outer surface of each strut. However, then the concentration at the tissue adjacent to the struts may exceed $C_{max}$.

Figure 1:
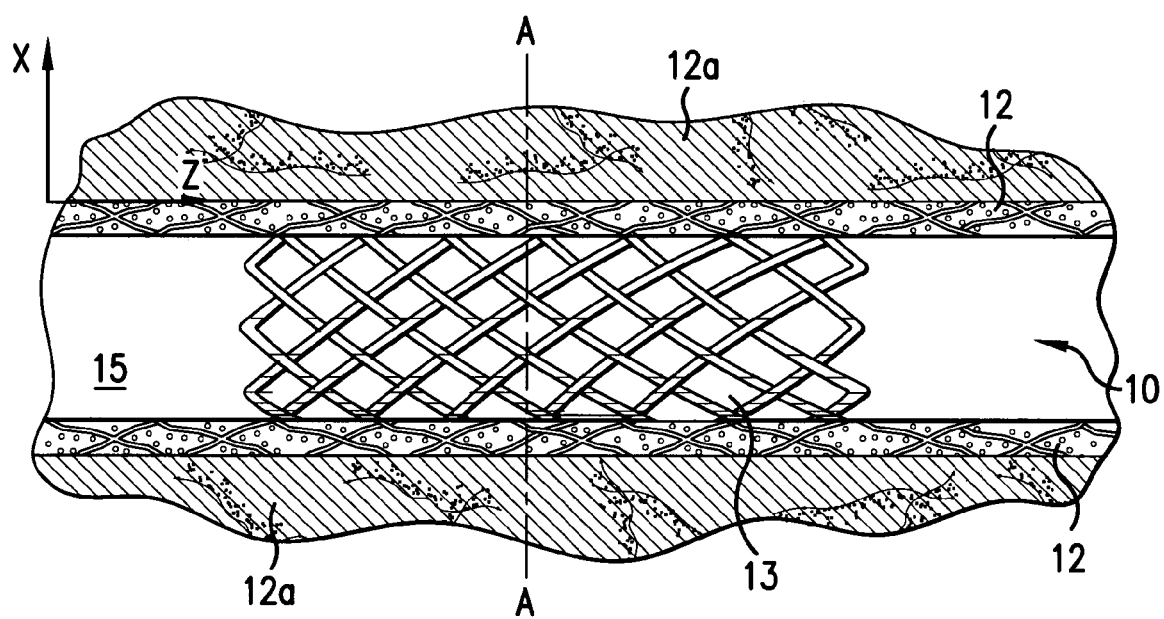
FIG. 1 depicts a side view of a stent without non-structural elements in a cross-sectioned blood vessel. The stent is coated with a biologically active material.
Figure 2A:
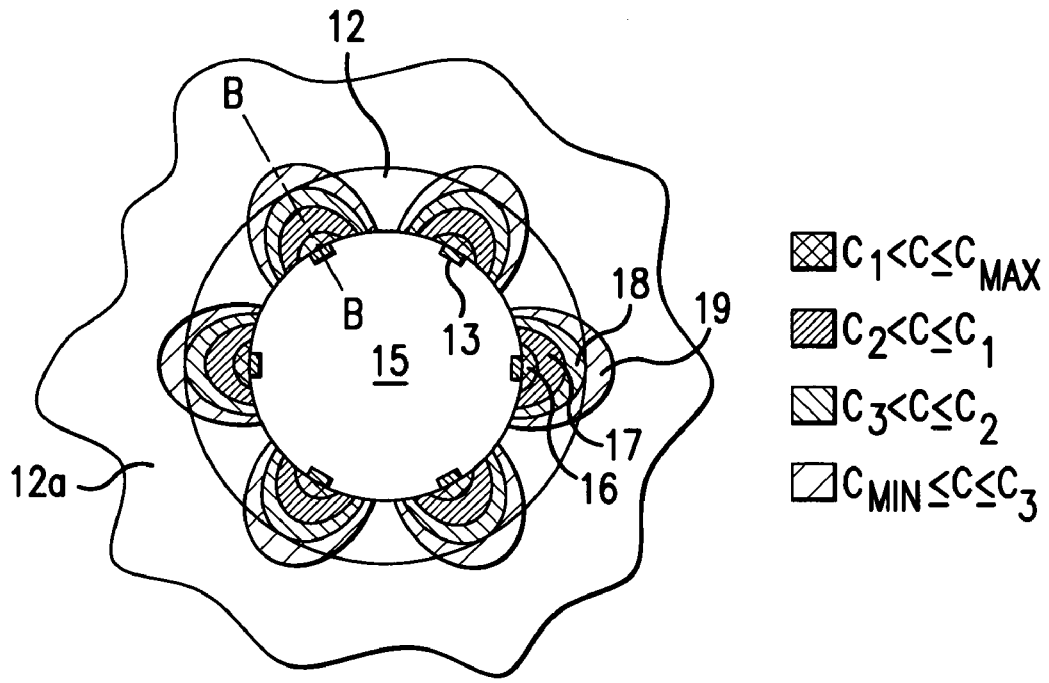
FIGS. 2A and 2B depict cross sectional views of the stent and blood vessel of FIG. 1 along line A-A and line B-B (shown in FIG. 2A), respectively.
Figure 2B:
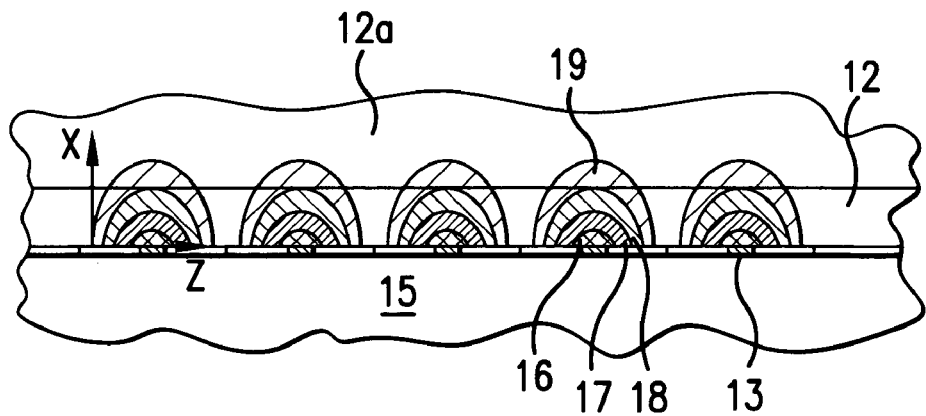

For example, FIG. 1 depicts a coated stent 10 having a conventional geometric pattern, which is placed in a blood vessel 15 having a vessel wall 12 to be treated. The biologically active material coated on struts 13 of the stent 10 is released into the vessel wall 12 to be treated. FIGS. 2A and 2B show cross sectional views along line A-A and line B-B (shown in FIG. 2A) of the stent 10 in FIG. 1 and the concentration levels of the biologically active material in each area surrounding the struts 13 at a certain time after the stent 10 was inserted into the vessel 15. The area adjacent to the struts, i.e., the area between the struts 13 and line 16 has a concentration level at or below $C_{max}$, which is just below the toxic level. The farther from the struts 13 the area is located, the lower the concentration becomes. Thus, the concentration levels gradually decrease from the area between lines 16 and 17, the area between 17 and 18, to between 18 and 19. The area between line 18 and line 19 has a concentration level at or higher than $C_{min}$. A concentration of the biologically active material in the area outside line 19 is below $C_{min}$, and thus the pharmacological effects of the biologically active material does not result in the area.

Furthermore, FIGS. 2A and 2B clearly show that there are gaps between each strut 13, i.e., near the center of cells, wherein the vessel wall to be treated does not receive sufficient biologically active material to have $C_{min}$. The size of the area within line 19, i.e., the areas having the concentrations above $C_{min}$, may be increased to include the entire area of the vessel wall to be treated 12 if the amount of the biologically active material on the struts 13 is increased. However, by doing so, the area adjacent to the struts 13 may be also increased and exceed the toxic level. Therefore, there is a need for a medical device that can ensure the concentration of the biologically active material throughout the body tissue to be treated is at least $C_{min}$ and at most $C_{max}$.

To achieve such a desired distribution of a biologically active material throughout the body tissue to be treated, the embodiments of the medical device of the present invention comprise a plurality of struts and a plurality of non-structural elements integral to the struts. The struts and non-structural elements comprise the biologically active material. These non-structural elements are used to adjust the distribution of the biologically active material in the body tissue so that the desired concentration-profile for the biologically active material released from the medical device into the body tissue can be achieved. For instance, the medical device of the present invention can achieve concentrations higher than $C_{min}$ at the tissue located at the center of cells without increasing the local concentration at an area adjacent to the struts higher than $C_{max}$.

Figure 3:
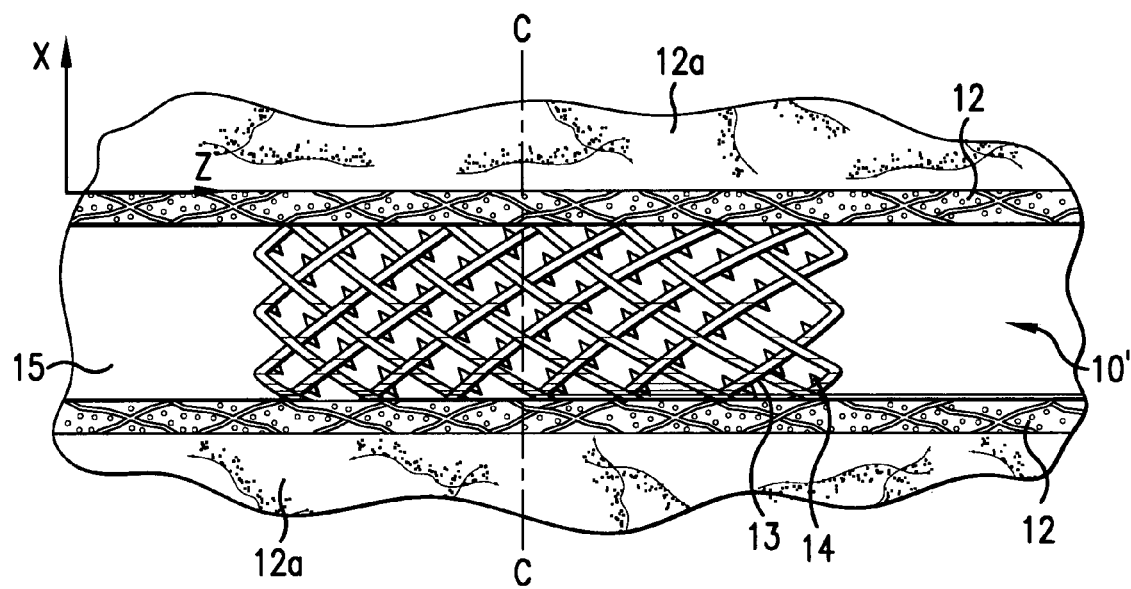
FIG. 3 depicts a side view of a stent with non-structural elements in a cross-sectioned blood vessel. The stent is coated with a biologically active material.
Figure 4A:
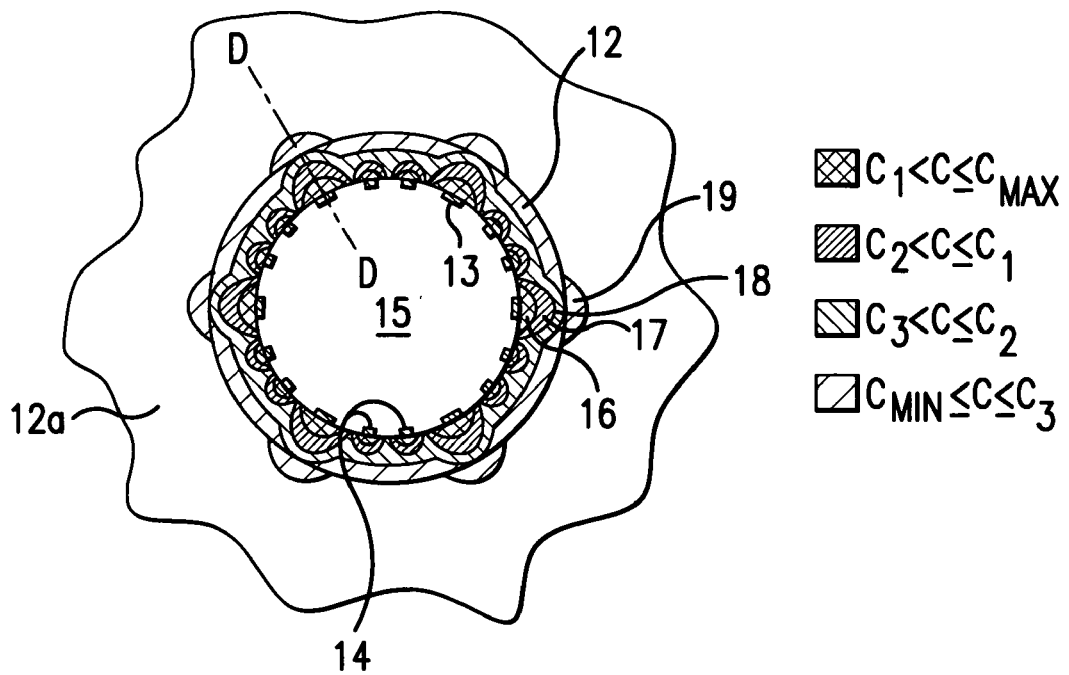
FIGS. 4A and 4B depict cross sectional views of the stent and blood vessel of FIG. 3 along line C-C and line D-D (shown in FIG. 4A), respectively.
Figure 4B:
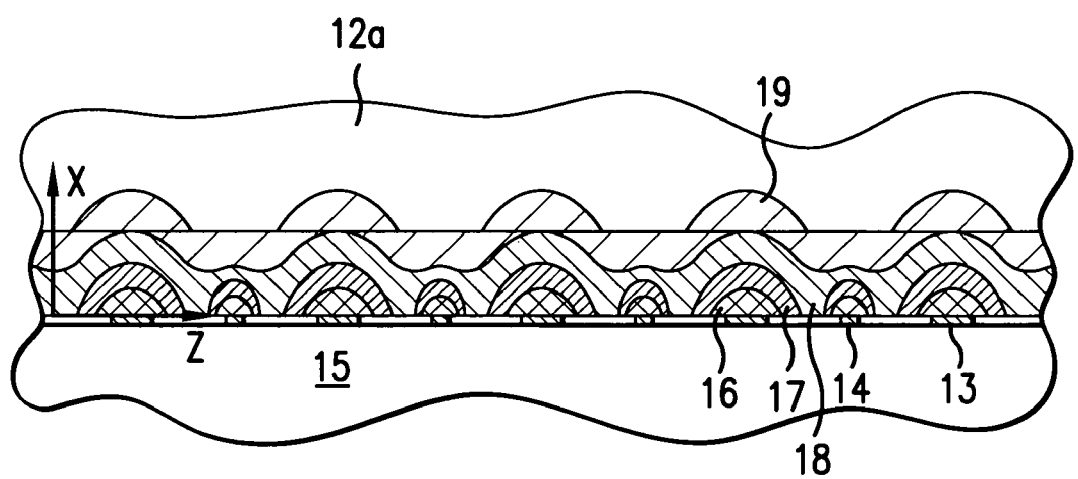

An example is shown in FIGS. 3, 4A and 4B. FIG. 3 depicts a coated stent 10' which is obtained by modifying the conventional geometric pattern of stent 10 shown in FIG. 1 by incorporating non-structural elements 14 integral to the struts 13. The stent 10' is placed in a blood vessel 15 having a vessel wall 12 to be treated. The biologically active material coated on struts 13 and non-structural elements 14 of the stent 10' is released into the vessel wall 12 to be treated and tissue 12a surrounding the vessel wall 12. FIGS. 4A and 4B show cross sectional views along line C-C and D-D (shown in FIG. 4A) B of the stent 10' in FIG. 3 and the concentration levels of the biologically active material in each area surrounding the struts 13 and the nonstructural elements 14 at a certain time after the stent 10' was inserted in the vessel 15. The area adjacent to the struts, i.e., the area between the struts 13 or the nonstructural elements 14 and line 16 has a concentration level from at or below $C_{max}$, which is just below the toxic level. The farther from the struts 13 or the nonstructural elements 14 the area is located, the lower the concentration becomes. The area between line 18 and line 19 has the concentration level at or higher than $C_{min}$. FIG. 4 clearly shows that the stent 10' can achieve concentrations higher than $C_{min}$, throughout the entire area of the vessel wall to be treated 12, even at areas located at the center of cells, without increasing the concentration at areas adjacent to the struts above $C_{min}$.

The term "non-structural element" refers to an element integral with a strut, which can project from the strut or can be located along the strut. Such non-structural elements have substantially no effect on the mechanical properties of the struts, such as, for example, (1) radial strength, (2) longitudinal flexibility, (3) expansion ratio, (4) contractibility and (5) profile of a medical device comprising the plurality of struts. In embodiments of the medical device of the present invention, the non-structural elements are integral with the struts, namely, they are generally made from the same material as the struts and are formed as a continuous part of the struts. Preferably, the non-structural elements and struts may be manufactured simultaneously; for example, struts having non-structural elements can be laser-ablated from a plate of metal or polymer.

Figure 5:
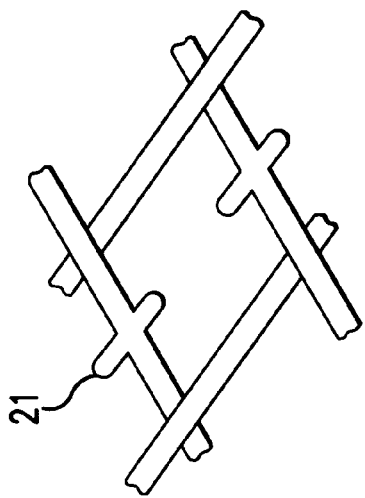
FIG. 5 depicts struts of a conventional expandable stent.
Figure 6:
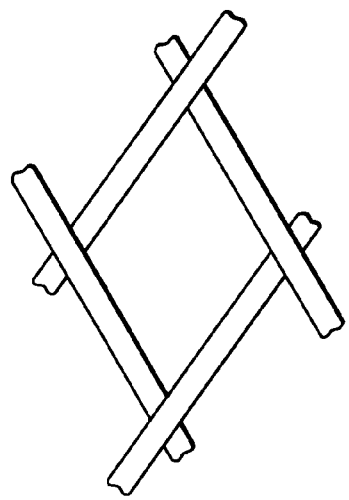
Figure 9:
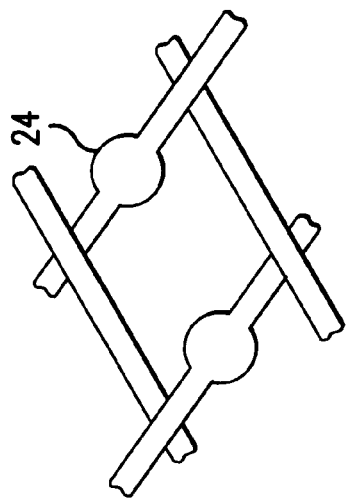
Figure 8:
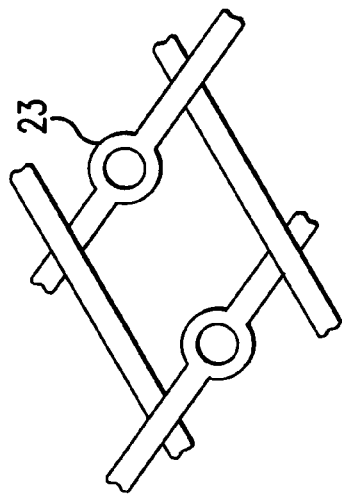
Figure 7:
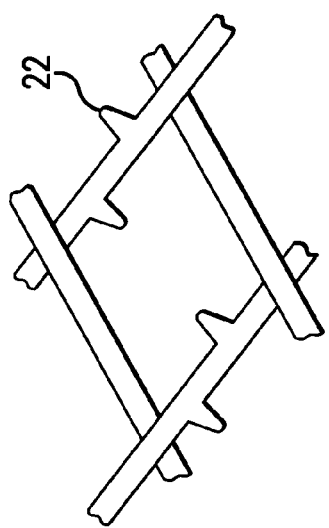
Figure 11:
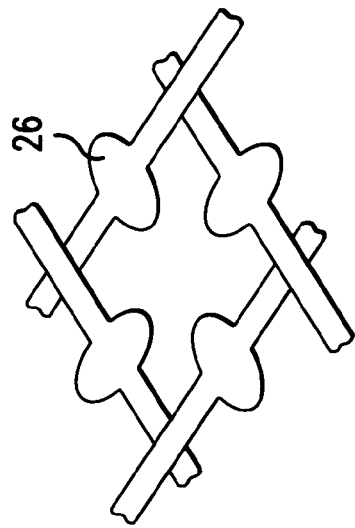
Figure 10:
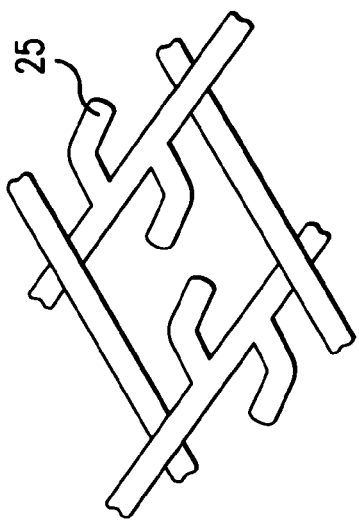
Figure 14:
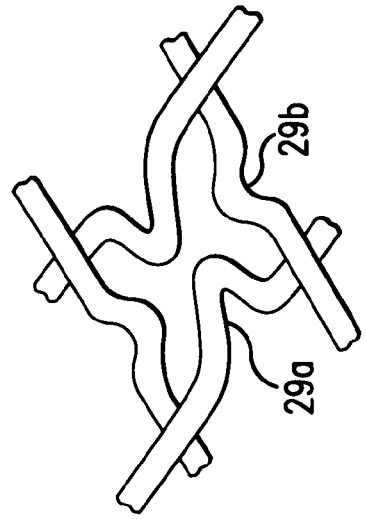
Figure 13:
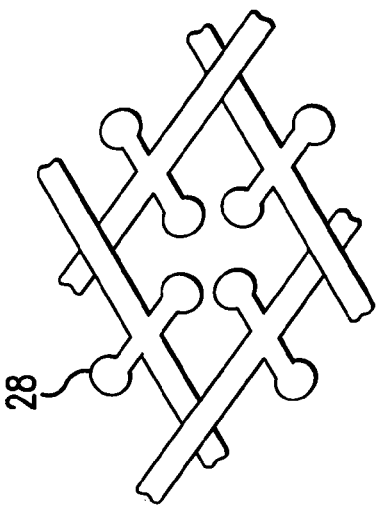
Figure 12:
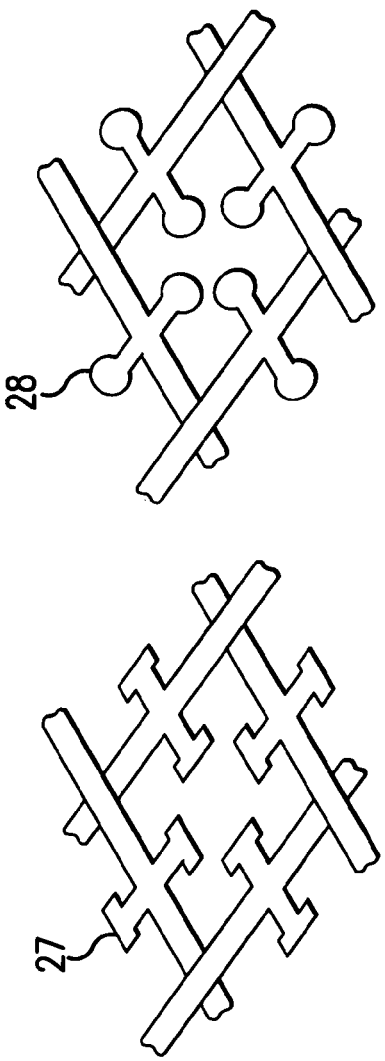

FIG. 5 depicts example of conventional struts without non-structural element, and FIGS. 6-14 depict examples of non-structural elements integral with the conventional struts. Shapes of the non-structural elements include, but not limited to, a straight rod (21 in FIG. 6), a cone (22 in FIG. 7), a truncated cone (not shown), a hoop (23 in FIG. 8), a knot (24 in FIG. 9), a bent rod (25 in FIG. 10), an oval (26 in FIG. 11), and a rod having heads at its ends (27 in FIGS. 12 and 28 in FIG. 13). Bends in the struts (29a and 29b in FIG. 14) can be used as non-structural elements so long as they do not affect the mechanical properties of the struts.

This embodiment of the medical device of the present invention can be used for delivering any kind of biologically active material. Preferably, the biologically active material is hydrophobic, e.g., paclitaxel, actinomycin, sirolimus, tacrolimus, everolimus, dexamethasone, halofuginone, and hydrophobic nitric oxide adducts. Other examples of the biologically active material, coatings containing the biologically active material, and examples of the medical device are explained later in this application.

5.1.2. Designing Medical Devices Having Struts and Non-Structural Elements

The present invention is directed to a method for designing a medical device comprising a plurality of struts and non-structural elements integral with the struts for delivering a biologically active material to a body tissue of a patient. As explained above, when the struts are placed in a certain geometric pattern, the concentration of a biologically active material at a center of each cell may not reach $C_{min}$ of the biologically active material. However, the method of the present invention provides a geometric pattern of the struts in which the concentration of a biologically active material above $C_{min}$ can be achieved throughout the body tissue to be treated without increasing the concentration at the tissue located adjacent to the struts above $C_{max}$.

In the method of the invention, a preliminary medical device comprising a plurality of struts in a geometric pattern is modified by incorporating non-structural elements to the struts to improve the concentration-profile for the biologically active material released from the device to the body tissue to be treated. Any medical device comprising a plurality of struts in a geometric pattern, such as stent, can be used as a preliminary medical device for the method of the invention provided that the struts comprises a biologically active material.

In the method of the present invention, a concentration-profile for the biologically active material delivered to the body tissue from the preliminary medical device is determined. From this profile, the areas of tissue in which the concentration of the biologically active material is below $C_{min}$ can be determined. Such areas are then correlated to the parts of the geometric pattern of the struts of the preliminary medical device that were in contact with or near such areas.

The determination of such concentration-profile can be conducted by actually measuring concentrations using the biologically active material in vitro with a tissue model, which is similar to the body tissue to be treated, such as cannulated animal arteries with surrounding tissue or an artificial tissue, or in vivo with an animal model, such as rabbits, guinea pigs, or pigs. The biologically active material used for the experiment may be labeled with a fluorescence, a radioactive material or dye or can be assayed by tissue digestion and analyzed by HPLC. Such labeled biologically active material is coated on the medical device, and then the coated medical device is inserted into the tissue model, or artificial tissue, or implanted in an animal. Alternatively, the biologically active material may be detected using standard HPLC separation, mass spectroscopy or other direct analytical methods. After insertion, the tissue may be appropriately sectioned, and the concentration-profile for the labeled biologically active material is measured by a means appropriate to the label employed for the experiment. However, a necessary care should be taken that the label would not greatly affect the diffusion of the biologically active material itself.

However, the concentration-profile may also be determined by mathematical simulation. For example, such simulation can be conducted by using the following conditions and equations:

$$\frac{\partial C}{\partial t} = D_x\left(\frac{\partial^2 C}{\partial x^2}\right) + D_z\left(\frac{\partial^2 C}{\partial z^2}\right)$$

wherein C refers to a concentration of the biologically active material in the body tissue, x refers to a distance from the medical device along x axis which is perpendicular to a boundary between the medical device and the body tissue, z refers to a distance from the medical device along z axis which is parallel to the boundary, Dx refers to a diffusion coefficient of the biologically active material in direction along x axis, Dz refers to a diffusion coefficient of the biologically active material in a direction along z axis. For example, such x axis and z axis are shown in FIGS. 1, 2B, 3 and 4B. Dx and Dz can be determined by the experiments using the labeled biologically active material in vitro or in vivo as described above. C=0 at t=0, wherein boundary conditions are as follows:

(i) at a common boundary between the struts and the body tissue (at x=0):

$$D_x \frac{\partial C}{\partial x} = h_1(C - C_\Gamma)$$

wherein $C_\Gamma$ refers to a concentration of the biologically active material in the struts, and $h_1$ refers to a mass transfer coefficient. Value of $h_1$ can be determined by the same experiments described above or determined by assumption based on the information known to one skilled in the art;

(ii) at a boundary between blood flow and the body tissue (at x=0):

$$D_x \frac{\partial C}{\partial x} = h_2(C - 0)$$

wherein $h_2$ refers to another mass transfer coefficient. Value of $h_2$ can be determined by the same experiment mentioned above or determined by assumption based on the information known to one skilled in the art;

(iii) at an adventitial side of vascular wall (at x=L):

$$D_x \frac{\partial C}{\partial x} = -h_3(C - 0)$$

wherein $h_3$ is yet another mass transfer coefficient, and L is a width of a region of interest. Value of $h_3$ can be determined by the same experiment mentioned above or determined by assumption based on the information known to one skilled in the art; and (iv) "symmetry" (no-flux) boundary conditions at certain cross-sections perpendicular to z axis:

$$\frac{\partial C}{\partial z}(z=0) = \frac{\partial C}{\partial z}(z=L_z) = 0$$

wherein Lz is the length along z axis of a region of interest.

Although a simplified model based on two diffusion coefficients of the biologically active material in two directions, i.e., depth of the tissue penetration and the distance diffused, is described above as an example, there are more complex models can be also employed for the method of the present invention. Such complex models may further account for other variables, such as convection, vessel wall inhomogenetics, the type of cells, the lesions, the variabilities brought by different coatings or coating porosity, blood flow, body temperature, blood pressure, and/or pressure of the implant against the vessel wall.

Subsequent to determining the concentration-profile for the biologically active material which is released from the preliminary medical device, the geometric pattern of the preliminary medical device is modified by incorporating a plurality of non-functional elements that are integral with the struts to achieve more desired distribution of the biologically active material in the body tissue to be treated. The non-structural elements also comprise the biologically active material. For example, the area of tissue in which the concentration of the biologically active material is below $C_{min}$ is determined from the concentration-profile. Then, it is determined which parts of the geometric pattern of the struts of the preliminary medical device were in contact with or near such areas. The non-structural elements can be incorporated near such parts in the geometric pattern, so that the biologically active material released from the non-structural elements would change the concentration in those areas.

For example, a stent 10 having a plurality of struts 13 in a conventional geometric pattern in FIG. 1 can be provided as the preliminary medical device. The struts 13 are coated with a biologically active material. Then, a concentration-profile in a body tissue for the biologically active material which is released from the struts 13 is determined. An example of such profile is shown in FIGS. 2A and 2B with the cross-sectional views of the stent 10 in the blood vessel 15. The determination of such concentration-profile can be conducted by actually measuring concentrations or by mathematical simulation as mentioned above. According to the obtained concentration-profile, the geometric pattern of the struts 13 of the preliminary stent 10 are modified with non-structural elements 14, for example, as shown in FIG. 3. FIGS. 4A and 4B show the concentration-profile for the biologically active material in the blood wall 12. When the concentration-profile in the vessel wall to be treated 12 shown in FIGS. 2A-B and 4A-B are compared, in FIGS. 4A-B, the concentrations generally throughout the entire area of the vessel wall to be treated 12 are above $C_{min}$ and below $C_{max}$. It is clear that the modified stent 10' achieves a more desirable concentration-profile in the vessel to be treated 12 with the biologically active material than the preliminary stent 10.

Preferably, after a concentration-profile for the biologically active material in the body tissue which is released from the modified preliminary medical device is determined, if there is an area of the body tissue having the local concentration of the biologically active material lower than $C_{min}$, then the device is modified again by adding non-structural elements to the struts. In addition to or instead of merely adding additional non-structural elements, the non-structural elements which have been already added can be removed or relocated according to the determined concentration-profile. Consequently, a medical device having further improved delivery of the biologically active material is obtained. If necessary, the determination step and the modification step explained above can be repeated as many as possible.

5.1.3. Medical Device with Radially Asymmetric Area Having Non-Structural Elements The prior sections (section 5.1.1 and 5.1.2) explained how non-structural elements can be added to a preliminary medical device to achieve a more desired concentration-profile for the biologically active material released from the device into body tissue. When the entire outer surface of a medical device, which comprises the plurality of struts and non-structural elements, is used to treat body, the non-structural elements should be positioned uniformly throughout the entire outer surface of the medical device.

However, if the body tissue to be treated is smaller in surface area than the entire outer surface of the medical device, then the non-structural elements do not have to be positioned throughout the entire surface of the medical device. For example, the medical device can comprise a tubular portion comprising an outer surface, such as a stent, which comprises a plurality of struts and a plurality of non-structural elements. The non-structural elements located in a radially asymmetric distribution, such as shown in FIG. 17 where 33 represents the location of the non-structural element on outer surface of a simplified figure of a stent 32. In this figure, the non-structural elements are distributed only in a rectangular portion of the outer surface. FIG. 18 depicts a stent wherein non-structural elements are provided onto the struts only in a rectangular portion of the outer surface. Such rectangular portion may be parallel to longitudinal axis of the tubular portion and may have the same length as that of the tubular portion. The rectangular portion is preferably from about 10% to about 90% of the entire outer surface.

The present invention is also directed to a method for delivering a biologically active material to body tissue using the above-mentioned medical device, which comprises a tubular portion comprising an outer surface which comprises a plurality of struts and a plurality of non-structural elements, and the non-structural elements are located in a radially asymmetric distribution on the outer surface. In the method, the medical device is inserted into body of the patient. Preferably, the non-structural elements are distributed only in a rectangular portion of the outer surface, and the medical device is inserted in such a way that the rectangular portion is in direct contact with the body tissue to be treated. In this way, the body tissue to be treated will receive desired distribution of the biologically active material. On the other hand, the body tissue which does not need to be treated will be exposed to a lesser amount of the biologically active material.

5.2. Increased Capacity of the End Sections for Carrying or Containing a Biologically Active Material In other embodiments of the medical device insertable into the body of a patient of the invention, the medical device comprises an outer surface comprising a plurality of struts, and the end sections of the outer surface have a greater capacity per unit length of the outer surface for carrying or containing a biologically active material than the middle section of the outer surface. Specifically, in one embodiment of the medical device, each strut at the end sections has greater available surface area per unit length of the outer surface than the middle section. In another embodiment, the end sections have a greater affinity for the biologically active material per unit length of the outer surface than the middle section.

The medical device of the present invention may be manufactured with or without a biologically active material by a manufacturer. When the medical device of the present invention is manufactured without a biologically active material, a practitioner (e.g., a medical doctor or a nurse) can apply the biologically active material to the medical device. In either case, since the end sections of the outer surface have a greater capacity per unit length of the outer surface for carrying or containing the biologically active material than the middle section, the end sections will carry a greater amount of the biologically active material when the biologically active material is applied to the medical device without needing to change application method of the biologically active material to the end sections and the method to the middle section. Therefore, when a practitioner applies to the outer surface of the medical device, such as by dipping, a coating composition containing a biologically active material, a larger amount of the biologically active material per unit length of the outer surface will be deposited at the end sections than the middle section.

The term "unit length of the outer surface" refers to the length on an imaginary straight line along the outer surface drawn between a point on an edge of the outer surface and another point on the opposing edge of the outer surface. Therefore, the terms, such as "capacity per unit length of the outer surface," "available surface area per unit length of the outer surface," and "amount per unit length of the outer surface," refer respectively to the capacity, available surface area and amount per unit length of the imaginary straight line explained above.

5.2.1. Increased Available Surface Area at the End Sections

As explained above, one of the embodiments of the medical device has end sections which have greater available surface area per unit length of the outer surface than that of the middle section. The term "available surface area" refers to a surface area which is available to be coated by a coating composition comprising a biologically active material.

One way of increasing the available surface area of the end sections is to fabricate the outer surface of the medical device using more material at its ends. For example, when the medical device is comprised of struts, the available surface area per unit length of the outer surface in the end sections is increased by adding non-structural elements to the struts. The non-structural elements are explained above (see section 5.1.1). The end sections comprise a greater number of the non-structural elements per unit length of the outer surface than the middle section. The middle section may have smaller number of the non-structural elements or no non-structural elements.

Further, the available surface area can be increased by increasing the surface area of the struts themselves. For example, wavy struts 30 shown in FIG. 15 can have more outer surface area per length than straight struts show in FIG. 5. Also, struts having greater average diameter, such as struts which are thicker or wider at certain portion 31 shown in FIG. 16, have greater outer surface area per length than struts which have smaller average diameter. Moreover, the end sections of the outer surface can be made to have greater available surface area by roughing the struts' outer surface or providing indentations or grooves on the struts' surface. The above-mentioned wavy struts, wider or thicker struts, indentations and grooves may have various shapes, so long as such structure does not affect stent's structural functions. For example, the above-mentioned structure should not hinder self-expansion of a self-expanding stent and should not cause any harm to the patient body. The above-mentioned wavy struts, indentations and grooves can be manufactured by laser ablation.

In another embodiment in which the capacity of the end sections to carry or contain the biologically active material is greater than the capacity of the middle section, the end sections of the outer surface are more porous, and the middle section of the surface is relatively less porous. The middle section may also be non-porous. For example, in FIG. 19, the circles 45 and 47 show enlarged portions of the outer surface of the struts 42 of a stent 40 in the middle section 44 and end section 46, respectively. The surface of the struts in the end section 46 has more pores 48 than the surface of the struts at the middle section 44. In such embodiment, the end sections 46 have a greater available surface area per unit length of the outer surface than that of the middle section 44 since the pores 48 increase available surface area.

The end sections of the outer surface may be made porous by forming the end sections of the outer surface themselves from a porous material or by forming the end sections with a non-porous material and then covering the end sections with a porous coating layer. For example, porous metal struts can be prepared by sintering metal, i.e., molding or pressing metal particles into a desired shape and heating them to a temperature slightly below the melting point of the metal. Porosity can be changed by using different particle sizes and/or dimensions and/or different temperatures. Also, porous metal struts can be prepared by using metal filaments or fibers. See e.g. U.S. Pat. No. 5,843,172 issued to Yan which discloses examples of struts made of porous materials, which is incorporated herewith by reference.

The end sections of the outer surface may be made porous by coated with a porous coating layer. A porous coating layer may be prepared, for example, by applying a mixture of a polymer, an elutable particulate material and a solvent on a surface to form a layer, and then eluting the elutable particulate material from the layer. The following is a detailed description of suitable materials and methods useful in producing a porous coating layer of the invention.

Polymer(s) useful for forming the porous coating layer should be ones that are biostable, biocompatible, particularly during insertion or implantation of the device into the body and avoids irritation to body tissue. Examples of such polymers include, but not limited to, polyurethanes, polyisobutylene and its copolymers, silicones, and polyesters. Other suitable polymers include polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers. Since the polymer is being applied to a part of the medical device which undergoes mechanical challenges, e.g. expansion and contraction, the polymers are preferably selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. The polymer is selected to allow the coating to better adhere to the surface of the expandable portion of the medical device when it is subjected to forces or stress. Furthermore, although the porous coating layer can be formed by using a single type of polymer, various combinations of polymers can be employed.

The elutable particulate materials which can be incorporated into the polymer include, but not limited to, polyethylene oxide, polyethylene glycol, polyethylene oxide/polypropylene oxide copolymers, polyhydroxyethyl methacrylate, polyvinylpyrrolidone, polyacrylamide and its copolymers, salts, e.g., sodium chloride, sugars, and elutable biologically active materials such as heparin. The amount of elutable particulate material that is incorporated into the polymer should range from about 20% to 90% by weight of the porous coating layer. Furthermore, to increase the porosity of the coating layer applied to the end sections of the surface, a larger amount of the elutable particulate material can be used to form the porous coating layer at the end sections than are used to form the porous coating layer at the middle section. For example, the amount of the elutable particulate material may be from about 0% to about 40% for the porous coating layer covering the middle section, and about 50% to 90% for the porous coating layer covering at the end sections. Also, a more porous coating layer can be realized by using larger average particle size of the elutable material. For example, the particles may have an average particle size from 60-100 microns for porous coating layer covering the end sections and from 0 to about 30 microns for the porous coating layer covering middle section.

The solvent that is used to form the mixture or slurry of polymer and elutable particulate materials include ones which can dissolve the polymer into solution and do not alter or adversely impact the therapeutic properties of the biologically active material employed. Examples of useful solvents for silicone include tetrahydrofuran (THF), chloroform and dichloromethane. The composition of polymer and elutable particulate material can be applied to the portion of the medical device in a variety of ways. For example, the composition can be spray-coated onto the device or the device can be dipped into the composition. One of skill in the art would be aware of methods for applying the coating to the device.

The thickness of the porous coating layer can range from about 25 µm to 0.5 mm. Preferably, the thickness is about 30 µm to 100 µm. After the composition is applied to the device, it should be cured to produce a polymer containing the particulate material and to evaporate the solvent.

To elute the particulate material from the polymer, a solvent is used. The device can be soaked in the solvent to elute the particulate materials. Other methods of eluting the particulate are apparent to those skilled in the art. The choice of the solvent depends upon the solubility of the elutable particulate material in that solvent. For instance, for water-soluble particulate materials such as heparin, water can be used. For elutable particulate materials that can be dissolved in organic solvents, such organic solvents can be used. Examples of suitable solvents, without limitation, include ethanol, dimethyl sulfoxide, etc.

Another example of a method for preparing a porous coating is a catalyst-free vapor deposition of a coating composition comprising a polyamide, parylene or a parylene derivative. See U.S. Pat. No. 6,299,604 to Ragheb et al., which is incorporated herein by reference.

In another embodiment of the present invention, the surface including the end sections and middle section are covered with a same porous coating layer composition; but the porous coating layer is thicker at the end sections than at the middle section. For example, a porous coating layer is applied to the entire surface, and then another porous coating layer is applied to the end sections while the middle section is covered by a sheath. The thickness of the porous coating layer at the end sections may be from about 80 μm to about 0.5 mm, and that at the middle section may be from about 10 μm to 40 μm. Since there is more porous coating at the end sections, the end sections of the outer surface should have a greater capacity to carry or contain a biologically active material.

5.2.2. The End Sections with Greater Affinity for the Biologically Active Material In another embodiment of the medical device of the present invention, the end sections of the outer surface have a greater affinity for the biologically active material than the middle section. In particular, the end sections comprise a first matrix material and the middle section comprises a second matrix material. The first matrix material has a greater affinity for the biologically active material of interest than the second matrix material so that the end sections can carry or contain a larger amount of the biologically active material per unit length of the outer surface than the middle section. The end sections and the middle section of the outer surface may be formed from the first matrix material and the second matrix material, respectively. Preferably, the end sections of the outer surface and the middle section of the outer surface are formed of another material and then are covered with a coating comprising each of the matrix materials.

Generally, when a biologically active material used is a hydrophilic, e.g., heparin, then a matrix material comprising a more hydrophilic material has a greater affinity for the biologically active material than another matrix material that is less hydrophilic. When a biologically active material used is a hydrophobic, e.g., paclitaxel, actinomycin, sirolimus (RAPAMYCIN), tacrolimus, everolimus, and dexamethasone, then a matrix material that is more hydrophobic has a greater affinity for the biologically active material than another matrix material that is less hydrophobic.

Examples of suitable hydrophobic polymers include, but not limited to, polyolefins, such as polyethylene, polypropylene, poly(1-butene), poly(2-butene), poly(1-pentene), poly (2-pentene), poly(3-methyl-1-pentene), poly(4-methyl-1-pentene), poly(isoprene), poly(4-methyl-1-pentene), ethylene-propylene copolymers, ethylene-propylene-hexadiene copolymers, ethylene-vinyl acetate copolymers, blends of two or more polyolefins and random and block copolymers prepared from two or more different unsaturated monomers; styrene polymers, such as poly(styrene), poly(2-methylstyrene), styrene-acrylonitrile copolymers having less than about 20 mole-percent acrylonitrile, and styrene-2,2,3,3,-tetrafluoropropyl methacrylate copolymers; halogenated hydrocarbon polymers, such as poly(chlorotrifluoroethylene), chlorotrifluoroethylene-tetrafluoroethylene copolymers, poly(hexafluoropropylene), poly(tetrafluoroethylene), tetrafluoroethylene, tetrafluoroethylene-ethylene copolymers, poly(trifluoroethylene), poly(vinyl fluoride), and poly(vinylidene fluoride); vinyl polymers, such as poly(vinyl butyrate), poly(vinyl decanoate), poly(vinyl dodecanoate), poly(vinyl hexadecanoate), poly(vinyl hexanoate), poly(vinyl propionate), poly(vinyl octanoate), poly(heptafluoroisopropoxyethylene), poly(heptafluoroisopropoxypropylene), and poly(methacrylonitrile); acrylic polymers, such as poly (n-butyl acetate), poly(ethyl acrylate), poly(1-chlorodifluoromethyl)tetrafluoroethyl acrylate, poly di(chlorofluoromethyl)fluoromethyl acrylate, poly(1,1-dihydroheptafluorobutyl acrylate), poly(1,1-dihydropentafluoroisopropyl acrylate), poly(1,1-dihydropentadecafluorooctyl acrylate), poly (heptafluoroisopropyl acrylate), poly 5-(heptafluoroisopropoxy)pentyl acrylate, poly 11-(heptafluoroisopropoxy)undecyl acrylate, poly 2-(heptafluoropropoxy)ethyl acrylate, and poly(nonafluoroisobutyl acrylate); methacrylic polymers, such as poly(benzyl methacrylate), poly(n-butyl methacrylate), poly(isobutyl methacrylate), poly(t-butyl methacrylate), poly(t-butylaminoethyl methacrylate), poly(dodecyl methacrylate), poly(ethyl methacrylate), poly(2-ethylhexyl methacrylate), poly(n-hexyl methacrylate), poly(phenyl methacrylate), poly(n-propyl methacrylate), poly(octadecyl methacrylate), poly(1,1-dihydropentadecafluorooctyl methacrylate), poly(heptafluoroisopropyl methacrylate), poly(heptadecafluorooctyl methacrylate), poly(1-hydrotetrafluoroethyl methacrylate), poly(1,1-dihydrotetrafluoropropyl methacrylate), poly(1-hydrohexafluoroisopropyl methacrylate), and poly(t-nonafluorobutyl methacrylate); polyesters, such a poly (ethylene terephthalate) and poly(butylene terephthalate); condensation type polymers such as and polyurethanes and siloxane-urethane copolymers; polyorganosiloxanes, i.e., polymeric materials characterized by repeating siloxane groups, represented by $R_a SiO_{4-a/2}$, where R is a monovalent substituted or unsubstituted hydrocarbon radical and the value of a is 1 or 2; and naturally occurring hydrophobic polymers such as rubber.

Examples of suitable hydrophilic monomer include, but not limited to; (meth)acrylic acid, or alkaline metal or ammonium salts thereof; (meth)acrylamide; (meth)acrylonitrile; those polymers to which unsaturated dibasic, such as maleic acid and fumaric acid or half esters of these unsaturated dibasic acids, or alkaline metal or ammonium salts of these dibasic adds or half esters, is added; those polymers to which unsaturated sulfonic, such as 2-acrylamido-2-methylpropanesulfonic, 2-(meth)acryloylethanesulfonic acid, or alkaline metal or ammonium salts thereof, is added; and 2-hydroxyethyl(meth)acrylate and 2-hydroxypropyl(meth) acrylate.

Polyvinyl alcohol is also an example of hydrophilic polymer. Polyvinyl alcohol may contain a plurality of hydrophilic groups such as hydroxyl, amido, carboxyl, amino, ammonium or sulfonyl(—$SO_3$). Hydrophilic polymers also include, but are not limited to, starch, polysaccharides and related cellulosic polymers; polyalkylene glycols and oxides such as the polyethylene oxides; polymerized ethylenically unsaturated carboxylic acids such as acrylic, mathacrylic and maleic acids and partial esters derived from these acids and polyhydric alcohols such as the alkylene glycols; homopolymers and copolymers derived from acrylamide; and homopolymers and copolymers of vinylpyrrolidone.

The first matrix material and the second matrix material may be prepared using either a hydrophilic polymer or a hydrophobic polymer, or a blend of a hydrophobic polymer and a hydrophilic polymer in a chosen ratio. For example, when the biologically active material is hydrophilic, then the first matrix material may be prepared by blending from about 55% to about 100% hydrophilic polymer and from about 45% to about 0% hydrophobic polymer; and the second matrix material may be prepared by blending from about 55% to about 100% hydrophobic polymer and from about 45% to about 0% hydrophilic polymer. The first matrix material contains a greater amount of the hydrophillic polymer than the second matrix material. When the biologically active material is hydrophobic, then the first matrix material may be prepared by blending from about 55% to about 95% hydrophobic polymer and from about 45% to about 5% hydrophilic polymer; and the second matrix material may be prepared by blending from about 55% to about 95% hydrophilic polymer and from about 45% to about 5% hydrophobic polymer. The first matrix material contains a greater amount of the hydrophobic polymer than the second matrix material.

Again, the outer surface of the medical device of the present invention is, covered with each matrix material, i.e., the end sections with a first matrix material and the middle section with a second matrix material. A first matrix material composition may be prepared and applied by any method to a surface of a medical device to form a coating, such as spraying, dipping, rolling, and electrostatic deposition. Likewise, a second matrix material composition may be prepared and applied by such methods. The first matrix material composition may be applied to the end sections of the outer surface while the middle section is covered to prevent coating the middle section with the first matrix material. Then the second matrix material composition may be applied to the middle section while the end sections are covered. In another embodiment, the second material composition may be applied to the entire outer surface including the middle section and the end sections, then the first matrix material composition may be applied to the end sections while the middle section is covered.

After the matrix material compositions are applied to the outer surface, the surface should be cured to produce matrix material coatings. The thickness of the matrix material coating can range from about 25 μm to about 0.5 mm. Preferably, the thickness is about 30 μm to 100 μm.

5.2.3. The End Sections with Greater Amount of Chemical Linking Material to Carry or Contain the Biologically Active Material In yet another embodiment of the present invention, the capacity of the end sections of the outer surface for carrying or containing a biologically active material can be increased relative to that of the middle section by using an increased amount of chemical linking material to link the biologically active material to the end sections of the outer surface. Specifically, the middle section and end sections of the outer surface are covered with a chemical linking material, and the end sections carry or contain a larger amount of the linking material per unit length of outer surface than the middle section. The chemical linking material allows the biologically active material to attach to the outer surface.

"Linking materials" may be any material which can be coupled to a biologically active material by any bond that are known in the relevant art including but not limited to, Van der Waals force, ionic bond, covalent bond, hydrogen bond or chemical cross-linking.

For example, U.S. Pat. No. 5,356,433 to Rowland et al., discloses that polysaccharides can be immobilized onto metallic surfaces by applying an organosilane coating with amine functionality and then applying a polysaccharide using carbodiimide as a coupling agent. In the present invention, if the organosilane with amine functionality is used as a linking material, the amount of this material per unit length of the outer surface at the end sections is greater than that at the middle section. In that way, larger amount of a polysaccharide, which is a biologically active material, can coupled to the end sections.

Also, U.S. Pat. No. 5,336,518 to Narayanan et al. discloses that a polysaccharide can be immobilized on a surface by applying a coat of heptafluorobutylmethacrylate (HFBMA) by radiofrequency (RF) plasma deposition, creating functional groups on the surface by RF plasma with water vapor, and then applying the polysaccharide using carbodiimide. In the present invention, larger amount of HFBMA, a linking material, is applied to the end sections so that larger amount of a polysaccharide, a biologically active material can be coupled to.

5.3. Radially Asymmetric Medical Devices Having Increased Capacity for Carrying or Containing a Biologically Active Material

5.3.1. Medical Devices Having Non-Structural Elements Located in a Radially Asymmetric Distribution As explained above, one way to increase the capacity for carrying or containing a biologically active material of the medical device is to increase available surface area. In one embodiment of the medical device of the invention, the available surface area is increased in radially asymmetric manner along the entire outer surface, instead of only at the end sections. One such embodiment where the surface area is increased in a radially asymmetric manner by adding non-structural elements to the outer surface (as to non-structural elements, see section 5.1.3). For example, only a rectangular portion of the outer surface has the non-structural elements. Such rectangular portion may be parallel to longitudinal axis of the tubular portion and may have the same length as that of the tubular portion. The rectangular portion is preferably from about 25% to about 75% of the entire outer surface. Please see section 1.3 as to a method for delivering a biologically active material to body tissue using such medical device.

5.3.2. Medical Device Having Radially Asymmetric Increased Available Surface Area or Affinity Another embodiment of the medical device of the invention comprises a tubular portion comprising struts and having an outer surface. A portion of the outer surface has increased available surface or affinity for the biologically active material in such a way that the available surface area or affinity for the biologically active material is radially asymmetric. Please see prior section (section 5.3.1) as to examples of radially asymmetric distributions. Increased available surface area or increased affinity to the biologically active material can be achieved as explained in the prior sections (sections 5.2.1 and 5.2.2). Please see section 5.1.3 as to a method for delivering a biologically active material to body tissue using such medical device.

5.4. Suitable Medical Devices

The medical devices of the present invention are insertable into the body of a patient. Namely, at least a portion of such medical devices may be temporary inserted into or semi-permanently or permanently implanted in the body of a patient. Preferably, the medical devices of the present invention comprise a tubular portion which is insertable into the body of a patient. The tubular portion of the medical device need not to be completely cylindrical. For instance, the cross-section of the tubular portion can be any shape, such as rectangle, a triangle, etc., not just a circle.

The medical devices suitable for the present invention include, but are not limited to, stents, surgical staples, catheters, such as central venous catheters and arterial catheters, guidewires, cannulas, cardiac pacemaker leads or lead tips, cardiac defibrillator leads or lead tips, implantable vascular access ports, vascular or other grafts, intra-aortic balloon pumps, heart valves, cardiovascular sutures, total artificial hearts and ventricular assist pumps.

Medical devices which are particularly suitable for the present invention include any kind of stent for medical purposes, which are known to the skilled artisan. Suitable stents include, for example, vascular stents such as self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 4,733,665 issued to Palmaz, U.S. Pat. No. 4,800,882 issued to Gianturco, U.S. Pat. No. 4,886,062 issued to Wiktor and U.S. Pat. No. 5,449,373 issued to Pinchasik et al. A bifurcated stent is also included among the medical devices suitable for the present invention. In preferred embodiments, the stent suitable for the present invention is an Express stent. In specific embodiments, the stent is Express™ stent and Express 2™ stent (Boston Scientific Corporation, Natic, Mass.).

The medical devices suitable for the present invention may be fabricated from polymeric and/or metallic materials. Examples of such polymeric materials include polyurethane and its copolymers, silicone and its copolymers, ethylene vinyl-acetate, poly(ethylene terephthalate), thermoplastic elastomer, polyvinyl chloride, polyolephines, cellulosics, polyamides, polyesters, polysulfones, polytetrafluoroethylenes, acrylonitrile butadiene styrene copolymers, acrylics, polyactic acid, polyclycolic acid, polycaprolactone, polyacetal, poly(lactic acid), polylactic acid-polyethylene oxide copolymers, polycarbonate cellulose, collagen and chitins. Examples of suitable metallic materials include metals and alloys based on titanium (e.g., nitinol, nickel titanium alloys, thermo-memory alloy materials), stainless steel, platinum, tantalum, nickel-chrome, certain cobalt alloys including cobalt-chromium-nickel alloys (e.g., Elgiloy7 and Phynox7) and gold/platinum alloy. Metallic materials also include clad composite filaments, such as those disclosed in WO 94/16646.

The medical devices suitable for the present invention also have an outer surface, and the outer surface has end sections and middle section. The term "outer surface" refers to a surface of the medical devices which are to be exposed to body tissue. For example, the tubular structure shown in FIG. 20 is a simplified view of a stent 40. The outer surface of the stent is the surface that is in direct contact with the body tissue when the device is inserted into the body. In the case that the medical device is a stent 40 comprised of struts 42 as shown in FIG. 19, the "outer surface" of the stent refers to the surfaces of the struts which are to directly contact with the body lumen or tissue.

The term "end section" of the outer surface refers to that part of the surface which extends from an end or edge of the tubular portion up to about 25%, preferably from about 3% to about 20% of the entire length of the outer surface. For example, when the medical device is a stent 40 as shown in FIG. 19 or 20, the end section 46 of the outer surface is a ring-shape portion extending from the edge of the outer surface of stent having length e, which is up to 25% of the entire length a of the outer surface of stent. In FIGS. 19 and 20, the end sections are shown as the shaded portions 46.

The term "middle section" refers to the remainder of the outer surface that is surrounded by the end sections as defined above. For example, in FIG. 19 or 20, the middle section 44 is a ring-shape portion having length m, which is surrounded by the end sections.

5.5. Applying Biologically Active Material to the Outer Surface

As discussed earlier, the biologically active material can be applied to the embodiments described in sections 2.1 to 2.3 when the device is manufactured or later on by a medical professional shortly before the device is inserted into a patient. The biologically active material may be applied to the outer surface of the device obtained as in sections 1.1-1.3, 2.1-2.3 and 3.1-3.2, alone or in conjunction with other materials, such as a polymeric material. For example, in the embodiment where the end sections have a greater available surface area per unit length of the outer surface than the middle section, the biologically active material can be applied to the outer surface in a coating composition containing the biologically active material and a polymeric material. Specifically, a coating composition of biologically active material and polymeric material can be prepared and then applied to the outer surface. However, the biologically active material alone can also be applied to the outer surface of this embodiment.

In the embodiments where a portion of the outer surface has a greater affinity for the biologically active material or where a portion of the outer surface contains more chemical liking material, the biologically active material is preferably applied alone to the outer surface. For instance, in the embodiment having a matrix material with greater affinity for the biologically active material in a portion of the outer surface, the biologically active material can be applied to the matrix material coatings on the outer surface. However, the biologically active material can also be applied to the material along with a polymeric material. Also, the biologically active material can be incorporated into the matrix material coating compositions to form matrix material coatings that already containing biologically active material.

5.5.1. Coating Compositions and Coating Layers

The coating compositions suitable for the present invention can be applied by any method to a surface of a medical device to form a coating. Examples of such methods are spraying, dipping, rolling, electrostatic deposition and all modern chemical ways of immobilization of bio-molecules to surfaces.

The coating composition used in the present invention may be a solution of a biologically active material in an aqueous or organic solvent. Such coating composition may be applied to a surface, and the solvent may be evaporated. A biologically active material solution may be used when the tubular portion of the medical device has end sections having increased surface area or increased affinity as explained above, especially when the end sections are porous.

Furthermore, coating compositions useful for the present invention may include a polymeric material and optionally a biologically active material dispersed or dissolved in a solvent suitable for the medical device which is known to the skilled artisan. The solvents used to prepare coating compositions include ones which can dissolve the polymeric material into solution and do not alter or adversely impact the therapeutic properties of the biologically active material employed. For example, useful solvents for silicone include tetrahydrofuran (THF), chloroform, toluene, acetone, isooctane, 1,1,1-trichloroethane, dichloromethane, and mixture thereof.

A coating of a medical device of the present invention may consist of various kinds of combination of multiple coating layers. For example, the first layer and the second layer may contain different biologically active materials. Alternatively, the first layer and the second layer may contain an identical biologically active material having different concentrations. In one embodiment, either of the first layer or the second layer may be free of biologically active material. For example, when the biologically active solution is applied onto a surface and dried (the first layer), a coating composition free of a biologically active material (the second layer) can be applied over the dried biologically active material.

The polymeric material should be a material that is biocompatible and avoids irritation to body tissue. Preferably the polymeric materials used in the coating composition of the present invention include, but not limited to, polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate, styrene isobutylene copolymers and blends and copolymers thereof. Also, other examples of such polymers includes polyurethane (BAYHDROL®, etc.) fibrin, collagen and derivatives thereof, polysaccharides such as celluloses, starches, dextrans, alginates and derivatives, hyaluronic acid, and squalene. Further examples of the polymeric materials used in the coating composition of the present invention include are selected from the following: polyurethanes, silicones (e.g., polysiloxanes and substituted polysiloxanes), and polyesters. Other polymers which can be used include ones that can be dissolved and cured or polymerized on the medical device or polymers having relatively low melting points that can be blended with biologically active materials. Additional suitable polymers include, thermoplastic elastomers in general, polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl monomers, copolymers of vinyl monomers and olefins such as ethylene-methyl methacrylate copolymers, acrylonitrile-styrene copolymers, ABS (acrylonitrile-butadiene-styrene) resins, ethylene-vinyl acetate copolymers, polyamides such as Nylon 66 and polycaprolactone, alkyd resins, polycarbonates, polyoxymethylenes, polyimides, polyethers, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, EPDM (etylene-propylene-diene) rubbers, fluorosilicones, polyethylene glycol, polysaccharides, phospholipids, and combinations of the foregoing.

Preferred is polyacrylic acid, available as HYDROPLUS® (Boston Scientific Corporation, Natick, Mass.), and described in U.S. Pat. No. 5,091,205, the disclosure of which is hereby incorporated herein by reference. In a most preferred embodiment of the invention, the polymer is a copolymer of polylactic acid and plycaprolactone.

More preferably for medical devices which undergo mechanical challenges, e.g. expansion and contraction, the polymeric materials should be selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. Because of the elastic nature of these polymers, the coating composition adheres better to the surface of the medical device when the device is subjected to forces, stress or mechanical challenge.

A controlled-release coating of a biologically active material may be prepared by a coating composition comprising an appropriate hydrophobic polymer. For example, a controlled-release coating may comprise a coating layer containing a biologically active material and a top coating layer comprising a hydrophobic polymer. Also, a controlled-release coating may be prepared from a coating composition containing a mixture of a hydrophobic polymer and a biologically active material.

The amount of the polymeric material present in the coatings can vary based on the application for the medical device. One skilled in the art is aware of how to determine the desired amount and type of polymeric material used in the coating. Preferably, the amount of polymeric material ranges from about 1 to about 15 weight % of the coating composition. Preferably, the amount of polymeric material should be from about 1 to about 3 weight % of the coating composition.

After the composition is applied to the surface, it should be cured to produce a polymer containing the particulate material and to evaporate the solvent. Certain polymers, such as silicone, can be cured at relatively low temperatures, (e.g. room temperature) in what is known as a room temperature vulcanization (RTV) process. More typically, the curing/evaporation process involves higher temperatures so that the coated device is heated in a oven. Typically, the heating occurs at approximately 90° C. or higher for approximately 1 to 16 hours when silicone is used. For certain coatings the heating may occur at temperatures as high as 150° C. The time and temperature of heating will of course vary with the particular polymer, drugs, and solvents used. One of skill in the art is aware of the necessary adjustments to these parameters.

The thickness of the coating is not limited, but generally ranges from about 25 μm to about 0.5 mm. Preferably, the thickness is about 30 μm to 100 μm.

5.5.2. Suitable Biologically Active Material

The term "biologically active material" as used in the present invention encompasses therapeutic agents, drugs, genetic materials, and biological materials and can be used interchangeably with "biologically active material". Non-limiting examples of suitable therapeutic agent include heparin, heparin derivatives, urokinase, dextrophenylalanine proline arginine chloromethylketone (PPack), enoxaprin, angiopeptin, hirudin, acetylsalicylic acid, tacrolimus, everolimus, rapamycin (sirolimus), amlodipine, doxazosin, glucocorticoids, betamethasone, dexamethasone, prednisolone, corticosterone, budesonide, sulfasalazine, rosiglitazone, mycophenolic acid, mesalamine, paclitaxel, 5-fluorouracil, cisplatin, vinblastine, vincristine, epothilones, methotrexate, azathioprine, adriamycin, mutamycin, endostatin, angiostatin, thymidine kinase inhibitors, cladribine, lidocaine, bupivacaine, ropivacaine, D-Phe-Pro-Arg chloromethyl ketone, platelet receptor antagonists, anti-thrombin antibodies, anti-platelet receptor antibodies, aspirin, dipyridamole, protamine, hirudin, prostaglandin inhibitors, platelet inhibitors, trapidil, liprostin, tick antiplatelet peptides, 5-azacytidine, vascular endothelial growth factors, growth factor receptors, transcriptional activators, translational promoters, antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol lowering agents, vasodilating agents, agents which interfere with endogenous vasoactive mechanisms, antioxidants, probucol, antibiotic agents, penicillin, cefoxitin, oxacillin, tobranycin, angiogenic substances, fibroblast growth factors, estrogen, estradiol (E2), estriol (E3), 17-beta estradiol, digoxin, beta blockers, captopril, enalapril, statins, steroids, vitamins, taxol, paclitaxel, 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, 2'-O-ester with N-(dimethylaminoethyl)glutamide hydrochloride salt, nitroglycerin, nitrous oxides, nitric oxides, antibiotics, aspirins, digitalis, estrogen, estradiol and glycosides. In one embodiment, the therapeutic agent is a smooth muscle cell inhibitor or antibiotic. In a preferred embodiment, the therapeutic agent is taxol (e.g., Taxol®), or its analogs or derivatives. In another preferred embodiment, the therapeutic agent is paclitaxel, or its analogs or derivatives. In yet another preferred embodiment, the therapeutic agent is an antibiotic such as erythromycin, amphotericin, rapamycin, adriamycin, etc.

The term "genetic materials" means DNA or RNA, including, without limitation, of DNA/RNA encoding a useful protein stated below, intended to be inserted into a human body including viral vectors and non-viral vectors.

The term "biological materials" include cells, yeasts, bacteria, proteins, peptides, cytokines and hormones. Examples for peptides and proteins include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase (TIMP), cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells.

Other non-genetic therapeutic agents include:
  anti-thrombogenic agents such as heparin, heparin derivatives, urokinase, and PPack (dextrophenylalanine proline arginine chloromethylketone);
  anti-proliferative agents such as enoxaprin, angiopeptin, or monoclonal antibodies capable of blocking smooth muscle cell proliferation, hirudin, acetylsalicylic acid, tacrolimus, everolimus, amlodipine and doxazosin;
  anti-inflammatory agents such as glucocorticoids, betamethasone, dexamethasone, prednisolone, corticosterone, budesonide, estrogen, sulfasalazine, rosiglitazone, mycophenolic acid and mesalamine;
  anti-neoplastic/anti-proliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, cladribine, taxol and its analogs or derivatives;
  anesthetic agents such as lidocaine, bupivacaine, and ropivacaine;
  anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors, antiplatelet agents such as trapidil or liprostin and tick antiplatelet peptides;
  DNA demethylating drugs such as 5-azacytidine, which is also categorized as a RNA or DNA metabolite that inhibit cell growth and induce apoptosis in certain cancer cells;
  vascular cell growth promoters such as growth factors, vascular endothelial growth factors (VEGF, all types including VEGF-2), growth factor receptors, transcriptional activators, and translational promoters;
  vascular cell growth inhibitors such as anti-proliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;
  cholesterol-lowering agents, vasodilating agents, and agents which interfere with endogenous vasoactive mechanisms;
  anti-oxidants, such as probucol;
  antibiotic agents, such as penicillin, cefoxitin, oxacillin, tobranycin, rapamycin (sirolimus);

angiogenic substances, such as acidic and basic fibroblast growth factors, estrogen including estradiol (E2), estriol (E3) and 17-beta estradiol;

drugs for heart failure, such as digoxin, beta-blockers, angiotensin-converting enzyme (ACE) inhibitors including captopril and enalopril, statins and related compounds; and macrolides such as sirolimus or everolimus.

Preferred biological materials include anti-proliferative drugs such as steroids, vitamins, and restenosis-inhibiting agents. Preferred restenosis-inhibiting agents include microtubule stabilizing agents such as Taxol®, paclitaxel (i.e., paclitaxel, paclitaxel analogs, or paclitaxel derivatives, and mixtures thereof). For example, derivatives suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Other suitable therapeutic agents include tacrolimus; halofuginone; inhibitors of HSP90 heat shock proteins such as geldanamycin; microtubule stabilizing agents such as epothilone D; phosphodiesterase inhibitors such as cliostazole; Barkct inhibitors; phospholamban inhibitors; and Serca 2 gene/proteins.

Other preferred therapeutic agents include nitroglycerin, nitrous oxides, nitric oxides, aspirins, digitalis, estrogen derivatives such as estradiol and glycosides.

In one embodiment, the therapeutic agent is capable of altering the cellular metabolism or inhibiting a cell activity, such as protein synthesis, DNA synthesis, spindle fiber formation, cellular proliferation, cell migration, microtubule formation, microfilament formation, extracellular matrix synthesis, extracellular matrix secretion, or increase in cell volume. In another embodiment, the therapeutic agent is capable of inhibiting cell proliferation and/or migration.

In certain embodiments, the therapeutic agents for use in the medical devices of the present invention can be synthesized by methods well known to one skilled in the art. Alternatively, the therapeutic agents can be purchased from chemical and pharmaceutical companies.

5.5.3. Medical Devices with End Sections that Carry or Contain a Greater Amount of Biologically Active Material than the Middle Section In another embodiment of the invention, a more uniform release-profile for a biologically active material along the length of the outer surface of the medical device may be achieved by preparing a medical device having end sections that carry or contain a greater amount of a biologically active material than the middle section.

In section 2, supra, the medical devices of the present invention having end sections that have increased capacity for carrying or containing a biologically active material were explained. When a coating composition comprising the biologically active material is applied to such medical devices by a conventional method, such as spraying, dipping, rolling, and electrostatic deposition, the end sections will carry or contain a greater amount of the biologically active material per unit length of the outer surface than the middle section of the outer surface.

However, greater amounts of biologically active material at the end sections can also be achieved by controlling the amount of the biologically active material that is applied to the middle and end sections. For instance, additional coating composition containing a biologically active material can be applied to the end sections so that such sections have a thicker coating and hence contain more biologically active material. A method for preparing such medical device comprises, for example, applying a first coating composition containing a biologically active material to the end sections and a middle section of an outer surface, placing a cover over the middle section, applying more of the first coating composition or second coating composition to the end sections of the outer surface. The second coating composition may contain the same biologically active material as the first coating composition having the same or different concentration or may contain a different biologically active material.

Another example of a method useful in allowing more biologically active material to the end sections relative to the middle section involves covering the middle section. In particular, a coating composition containing the desired biologically active material is applied to the middle section and end sections. The middle section is then covered by a sheath or mesh. Such covering can be achieved also by masking using photolithography techniques. Additional coating composition is then applied to the end sections. The covering prevents such additional coating composition from being applied to the middle section so that the end sections will contain relatively more biologically active material.

In yet another embodiment of the medical device of the present invention, a greater amount of biologically active material can be applied to the end sections by applying coating compositions having different concentration of first biologically active material to the middle and end sections. For example, applying a coating composition containing a first concentration of a biologically active material is applied to the end sections while the middle section is covered. Thereafter, a second coating composition having a second concentration of biologically active material, which is smaller than the first concentration, to the middle section. The sections may be covered using sheaths or masking as explained above.

5.5.4. Medical Device Comprising a Biologically Active Material in a Radially Asymmetric Distribution Yet another embodiment of the medical device of the invention achieves a greater amount of release of a biologically active material to a necessary body tissue. Such medical device comprises an outer surface comprising the biologically active material in a radially asymmetric distribution. For example, a rectangular portion of the outer surface has a greater amount of the biologically active material than the rest of the outer surface. When the medical device comprises a tubular portion, the rectangular portion may be parallel to longitudinal axis of the tubular portion. The rectangular portion may be the same length as that of the tubular portion. A greater amount of the biologically active material can be distributed to a rectangular portion using any of the manners used to distribute a greater amount of the biologically active material to the end sections (see section 5.3, supra).

5.6. Barrier Layer over the Middle Section

In yet another embodiment, there is a barrier layer placed over the middle section of the outer surface, so that the end sections of the outer surface are allowed to release greater amounts of the biologically active material relative to the middle section. The middle and end sections are covered with a coating composition containing biologically active material. A covering or barrier layer is then placed over the middle section to limit the release of the biologically active material.

In this way, the release ratio of biologically active material from the end sections is relatively greater than from the middle section.

Examples of such barrier layers include, but not limited to, a top-coating layer covering the middle section. When the medical device of the present invention is a stent, examples of such barrier layers include, but not limited to, a sheath with or without apertures or openings. Suitable material for making such barrier layer include, but not limited to, hydrophobic polymers listed in section 2.2, supra.

5.7. Bands

In yet another embodiment of the medical device of the present invention, one or more bands are attached to an end section of a stent. A band is a strip-like piece of material that when connected to the stent is disposed in a manner concentric with the stent. For example, the band can be a cuff that attaches to the inner or outer surface of the stent sidewall. FIG. 21 shows a stent with a middle section 44 and end sections 46. Band 49a and 49b are attached to the end sections. At the outer end of each end section, i.e., the end further away from the middle section is an edge 50. The sidewall of the stent runs along the length of the stent. The sidewall may comprise a biologically active material.

FIGS. 21, 22 and 23 show variations of bands attached to end sections of a stent. FIG. 21 shows an embodiment in which bands completely surround an outer circumference of an end section. Alternatively the band can surround less than the entire circumference. As shown, the bands may be of any size or width or shape to best treat the area of injury. A band may be connected to the end section in a manner such that the band covers at most 10%, 20%, 30%, 40%, 50%, 60%, 70%, 80%, 90% or 98% of the outer surface of the end section.

As shown in FIG. 21, one band 49a covers only a portion of an end section 46. Another band 49b has an outer end 52, i.e., the end of the band that is further away from the middle section of the stent 44, that extends beyond the outer end of the end section upon which the band 49b is disposed. The inner end of the band is the end that is closer to the middle section of the stent sidewall.

FIG. 22 shows a portion of the band 52 having an outer end that extends axially beyond the edge 50 of the end section. The band has a tapered portion 51. This is beneficial for providing coverage of the distal tip of the expandable balloon beyond the edge of the stent. The tapered portion may be sized or shaped in any variation to best serve its purpose. A band may be attached to the edge 50 directly. The edge of an end section is the extreme end of each end section that is not adjacent the middle section. In FIG. 22, the band 52 is connected to the inner surface of the stent and rests along the inner surface of the end section. Again, the band may or may not extend axially beyond the edge of the end section, and may be of any size and shape.

FIG. 23 shows a stent made up of struts having bands 49 attached to the ends of the stent. The stent is shown implanted into a body lumen.

FIG. 24 shows a stent with bands 49 which covers less than the entire circumference of the end sections 46 of the stent. The bands 49 may be connected to the end sections on the outside surface or the inside surface of the end sections. In one embodiment, the portions of the end sections 46 may be removed to attach the bands 49 to the end sections 46 so that the bands 49 create a smooth continuous surface with the surface of the end sections 46. In another embodiment, the bands 49 may have a textured surface.

Any suitable materials may be used to make the bands as known in the art. Preferably, the bands are made from a polymeric materials, such as, but not limited to, any of the polymers listed in section 5.2.1. Preferably, the bands are made from an elastic material. Other suitable materials include ceramic and metallic materials. In addition, the material must be biocompatible.

The bands may be made by any suitable process, including, but not limited to, molding, extruding, casting, polymerization in molds, cross-linking, or weaving. Also, the bands can have a textured surface, the bands may not have a smooth surface. The texture can have a pattern such as a series of raised bumps.

Preferably, the bands comprise a radiopaque material. Any radiopaque materials may be use to make the bands radiopaque by any suitable method. For example, radiopaque materials may be absorbed, polymerized, extruded, or blended into the materials used to form the bands. In preferred embodiments, in order to facilitate detection of the bands via ultrasound, the bands may also comprise echogenic materials or other means for band location. This may or may not be done in combination with echogenic stents.

In addition, the bands may include therapeutic agents for treating tissue that lies beyond the ends of the stent. The bands provide additional surface area so that a greater amount of therapeutic agent may be delivered at the ends of the stent and/or to provide for radiopacity to be able to see more precisely the location of the stent during placement in the targeted site. In addition, the increased surface area provides added surface for drug loading. Moreover, the bands can accommodate a therapeutic agent with a large therapeutic index. Thus, a large dose range provide efficacy and have a wide tolerance for safety.

The bands may have different concentrations of the same therapeutic agent or different therapeutic agents in a variety of combinations. The therapeutic agents may be incorporated into the bands by any suitable method. For example, the therapeutic agents may be coated onto the bands. Also, a band may be coated with a composition comprising a therapeutic agent.

The bands could overlap the stent ends or be placed in close proximity to the stent ends. The amount of overlap may be determined in part by the area of injury to be treated. The bands may be of any desired dimensions. Preferably, the bands have a length of at least about 1 mm to at least about 10 mm. The length may be varied to adjust the amount of therapeutic agent. The length can be calculated in terms of the amount of material required to load a selected quantity of therapeutic agent onto the band. Preferably, the band extends to the end of the distal balloon so as to be in contact with any area of the stent or tissue that receives balloon dilation. In this sense, the band may be tapered to at least partially conform to the conical shape of the balloon end at the proximal end of the stent. Areas beyond the end of the balloon can be treated by drug diffusion. This is particularly helpful when the zone of biological injury extends beyond the reaches of any effective stent length and cannot be treated by drug delivery immediately adjacent to all afflicted areas.

The bands may be of any desired geometric configurations. For example, the bands may be cuff-like, or one or more bands may be positioned at the end of a stent. The bands may be cast over the end of the stent. Moreover, the bands may be used to provide directed diffusion. For example, the band could be formed such that a first therapeutic agent on the inner surface of the band could diffuse into the lumen, and a second therapeutic agent on the outer surface of the band could diffuse to the wall. The first and second therapeutic agents may or may not be the same. In an embodiment, the first band comprises an inner surface and an outer surface and that diffusion of a biologically active material is inhibited from the inner surface of the band. In another embodiment, different amounts of biologically active material may be released from the bands' outer surface compared to the bands' inner surface. The bands may comprise a biologically active material that is different or the same as the biologically active material of the sidewall.

The band may be constructed of multiple polymer layers so that the drug is loaded in a layer with high diffusivity and laminated with an impermeable barrier. The drug would only elute from the exposed surfaces of the laminate. The band may be constructed so that the drug elutes in a certain direction, such as the direction of the vessel wall, blood stream, or axially. The pH, ionic composition, hydrophobicity or hydrophilicity characteristics of the polymers can also be varied. By extending the bands beyond the ends of the stent, axial diffusion is facilitated by physically placing the drug loaded band past the stent.

The bands may be attached to the ends of the stent in various manners. For example, the band may be placed over the end of the stent or physically attached to the struts at the end of the stent with for example an adhesive. Other means of attachment could include sutures, thermal bonding, lamination of two layers such that the struts are captured between layers, and weaving of the band material into the structure of the stent.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

We claim:

1. A medical device comprising
   (i) a sidewall having a middle section, a first end section and a second end section;
   (ii) a first band comprising a first biologically active material, wherein the first band is connected to the first end section; and
   (iii) a second band connected to the second end section, wherein at least one of the bands only partially surrounds the circumference of the outer surface of one of the end sections.

2. The medical device of claim 1, wherein the first band further comprises a radiopaque material.

3. The medical device of claim 1, wherein the first band further comprises a polymeric material.

4. The medical device of claim 1, wherein the sidewall comprises a second biologically active material.

5. The medical device of claim 4, wherein the second biologically active material is coated onto the sidewall.

6. The medical device of claim 4, wherein the first band contains the first biologically active agent at a first amount and the second band contains the second biologically active agent at a second amount; wherein the first and second amounts are not equal.

7. The medical device of claim 1, wherein the first and second end sections each comprise an edge and the first band comprises an outer end; and wherein the first band is connected to the first end section in a manner such that the first band outer end extends axially beyond the first end section edge end.

8. A medical device comprising
   (i) a sidewall having a middle section, a first end section and a second end section;
   (ii) a first band comprising a first biologically active material,
   wherein the first band is connected to the first end section; the first and second end sections each comprise an edge and the first band comprises an outer end; the first band is connected to the first end section in a manner such that the first band outer end extends axially beyond the first end section edge end; and at least a portion of the first band outer end extending axially beyond the first end section edge is tapered.

9. The medical device of claim 8, wherein the first band further comprises a radiopaque material.

10. The medical device of claim 8, wherein the first band further comprises a polymeric material.

11. The medical device of claim 8, wherein the sidewall comprises a second biologically active material.

12. The medical device of claim 11, wherein the second biologically active material is coated onto the sidewall.

13. The medical device of claim 11, wherein the first band contains the first biologically active agent at a first amount and the second band contains the second biologically active agent at a second amount; wherein the first and second amounts are not equal.

14. A medical device comprising
   (i) a sidewall having a middle section, a first end section and a second end section;
   (ii) a first band comprising a first biologically active material, wherein the first band is connected to the first end section; and
   (iii) a second band comprising a second biologically active material connected to the second end section,
   wherein at least one of the bands comprises a plurality of layers, and wherein the first band contains the first biologically active agent at a first amount and the second band contains the second biologically active agent at a second amount; wherein the first and second amounts are not equal.

15. The medical device of claim 14, wherein the first band further comprises a radiopaque material.

16. The medical device of claim 14, wherein the first band further comprises a polymeric material.

17. The medical device of claim 14, wherein the second biologically active material is coated onto the sidewall.

18. The medical device of claim 14, wherein the first and second end sections each comprise an edge and the first band comprises an outer end; and wherein the first band is connected to the first end section in a manner such that the first band outer end extends axially beyond the first end section edge end.

19. A medical device comprising
   (i) a sidewall having a middle section, a first end section and a second end section;
   (ii) a first band comprising a first biologically active material, wherein the first band is connected to the first end section; and
   (iii) a second band connected to the second end section,
   wherein at least one of the bands comprises a plurality of layers, and wherein the first and second end sections each comprise an edge and the first band comprises an outer end; and wherein the first band is connected to the first end section in a manner such that the first band outer end extends axially beyond the first end section edge end.

20. The medical device of claim 19, wherein the first band further comprises a radiopaque material.

21. The medical device of claim 19, wherein the first band further comprises a polymeric material.

22. The medical device of claim 19, wherein the sidewall comprises a second biologically active material.

23. The medical device of claim 22, wherein the second biologically active material is coated onto the sidewall.

24. The medical device of claim 22, wherein the first band contains the biologically active agent at a first amount and the second band contains the second biologically active agent at a second amount; wherein the first and second amounts are not equal.

* * * * *